United States Patent [19]
Harrison et al.

[11] Patent Number: 5,830,848
[45] Date of Patent: Nov. 3, 1998

[54] METHOD AND AGENTS FOR INDUCEMENT OF ENDOGENOUS NITRIC OXIDE SYNTHASE FOR CONTROL AND MANAGEMENT OF LABOR DURING PREGNANCY

[75] Inventors: Michael R. Harrison; Michael A. Heymann, both of San Francisco; Robert Kirk Riemer, Half Moon Bay; Eileen Stack Natuzzi, San Francisco, all of Calif.

[73] Assignee: The Regents of the University of California, Oakland, Calif.

[21] Appl. No.: 450,126

[22] Filed: May 25, 1995

Related U.S. Application Data

[63] Continuation-in-part of Ser. No. 198,512, Feb. 18, 1994, Pat. No. 5,508,045, which is a continuation-in-part of Ser. No. 959,006, Oct. 9, 1992, abandoned.

[51] Int. Cl.⁶ .......................... A61K 38/19; A61K 38/22; A61K 45/65; C07K 14/435
[52] U.S. Cl. .......................... 514/2; 424/85.1; 424/85.2; 424/85.5; 530/399
[58] Field of Search .............................. 514/2; 424/85.1, 424/85.2, 85.5; 530/399

[56] References Cited

U.S. PATENT DOCUMENTS

| | | | |
|---|---|---|---|
| 4,402,942 | 9/1983 | Melin | 530/315 |
| 4,624,804 | 11/1986 | Voelter et al. | 514/12 |
| 5,061,690 | 10/1991 | Kann et al. | 530/324 |
| 5,134,120 | 7/1992 | Boyd et al. | 514/21 |
| 5,395,825 | 3/1995 | Feinberg et al. | 514/12 |
| 5,420,111 | 5/1995 | Gluckman et al. | 514/21 |
| 5,451,572 | 9/1995 | Cipolla et al. | 514/21 |

OTHER PUBLICATIONS

Yallampalli et al Endoerinology (1994) vol. 134 (4) pp. 1971–1974.

Hendrix et al Biology of Reproduction (1995) vol. 52, pp. 547–560.

Yallampalli et al, "Inhibition of Nitric Oxide Synthesis . . . " *AM. J. Obstet. Gynecol. 169*: 1316–1320 (1993).

Weiner et al, "Induction of Calcium–Dependent Nitrix Oxide Synthases . . . " PNAS 91(11): 5212–5216.

Dodds et al Attenuation of the Vasoconstrictor Effects of Thrombox Due . . . *AM. J. Obstet. Gynecol. 166(1)*: 224–230 *Jan. 1992).

J.R. Hemstad, et al., *Anesthesiology*, Effect of Nitrous Oxide on ICP Following Cranial–Dural Closure, vol. 73, No. 3A, p. A177, Sep. 1980.

Charles Weissman, et al., *Anesthesiology*, Determination of Hyper and Hypometabolism in the Postoperative ICU Patient, vol. 73, No. 3A, p. A306, Sep. 1980.

J. Leon, t al., *Anesthesiology*, Does Nitrous Oxide Affect Cerebral Blood Flow Velocity Under Neuroleptanesthesia in Children?, vol. 73, No. 3A, p. A389, page Sep. 1980.

G.B. Russell, et al., *Anesthesiology*, Hyperbaric Nitrous Oxide Anesthesia in Rats for Mac Determination, vol. 73, No. 3A, p. A399, Sep. 1980.

MS Pettis, et al., *Anesthesiology*, Nitrous Oxide and Coronary Artery Constriction in Pigs, vol. 73, No. 3A, p. A553, Sep. 1980.

WE Hoffman, et al., *Anesthesiology*, Fentanyl with Nitrous Oxide Does not Alter Cerebral Autoregulation or Blood Flow Compared to Unanesthetized Rats, vol. 73, No. 3A, p. A603, Sep. 1980.

T.S. Lee, et al., *Anesthesiology*, Inotropic Effects of Nitroglycerin, nitroprusside and Trimethaphan on Isolated Rabbit Myocardium, vol. 73, No. 3A, p. A629, Sep. 1980.

M. Palot, et al. *Anesthesiology*, Effects of Nitrous Oxide and/or Halothane on Cleavage Rate During General Anesthesia for Oocyte Retrieval, vol. 73, No. 3A, p. A930, Sep. 1980.

M. Yaster, et al., *Anesthesiology*, Interaction of Fentanyl and Nitrous Oxide on Cerebral and Peripheral Hemodynamics in Newborn Lambs, vol. 73, No. 3A, p. A1117, Sep. 1980.

D.O. Warner, et al., *Anesthesiology*, Nitrous Oxide Stimulates Expiratory Muscles in Dogs, vol. 73, No. 3A, p. 1172, Sep. 1980.

U. Pandit, et al., *Anesthesiology*, Nitrous Oxide Does Not Increase Postoperative Nausea/Vomiting in Pediatric Outpatients Undergoing Tonsillectomy–Adenoidectomy, vol. 73, No. 3A, p. A1245, Sep. 1980.

E.G. Carton, et al., *Anesthesiology*, Effects of Nitrous Oxide on Contractility and Relaxation of Isolated Mammalian Ventricular Myocardium, vol. 73, No. 3A, p. A1271, Sep. 1980.

M.J. Leroy, et al., *Biochemical Pharmacology*, Correlation Between Selective Inhibition of the Cyclic Nucleotide Phosphodiesterases and Contractile Activity in Human Pregnant Myometrium Near Term, vol. 38, No. 1, pp. 9–15, 1989.

Hidetaka Izumi, et al., *Am. J. Obstet Gynecol.*, Gestational changes in L–arginine–induced relaxation of pregnant rat and human myometrial smooth muscle, vol. 169, No. 5, pp. 1327–1337, 1993.

Chandrasekhar Yallampali, et al., *Am. J. Obstet. Gynecol.*, An L–arginine–nitric oside–cyclic guanosine monophosphate system exists in the uterus and inhibits contractility during pregnancy, vol. 170, pp. 175–185, 1993.

(List continued on next page.)

*Primary Examiner*—Stephen Walsh
*Assistant Examiner*—Daryl A. Basham
*Attorney, Agent, or Firm*—Hana Verny

[57] ABSTRACT

A method and agents for endogenous control, treatment, management and prevention of preterm labor by inducement of endogenous nitric oxide synthase. The method for endogenous production of nitric oxide in myometrium involves administering to a pregnant mammal a cytokine, hormone or growth factor agent able to induce production of nitric oxide or nitric oxide synthase. A non-invasive diagnostic procedure for detecting the presence and/or impending onset of premature labor.

20 Claims, 15 Drawing Sheets

OTHER PUBLICATIONS

E.S. Natuzzi, *Biochemical and Biophysical Research Communications,* Nitric Oxide Synthase Activity in the Pregnant Uterus Decreases at Parturition, vol. 194, No. 1, pp. 1–8, 1993.

David S. Warner, et al., *Anesthesiology,* Nitrous Oxide Does not Alter Infaret Volume in Rats Undergoing Reversible Middle Cerebral Artery Occlusion, vol. 73, pp. 686–693, 1990.

Dan Lawson, et al., *Anesthesiology,* Nitrous Oxide Effects on Isolated Myocardium: A Reexamination In Vitro, vol. 73, pp. 930–943. 1990.

Cotton, D.B., et al., "Role of Intravenous Nitroglycerin in the Treatment of Severe Pregnancy–Induced Hypertension Complicated by Pulmonary Edema", Dept. Obst. & Gyn. & Anesthes., Baylor Coll. of Med., vol. 154 1:91–94 (1985).

Kanji Nakatsu and Jack Diamond, "Role of cGMP in Relaxation of Vascular and Other Smooth Muscle", Can.J. Physiol., Pharmacol vol. 67:251–262 (1989).

Altabef, K.M., et al., "Intravenous Nitroglycerin for Uterine Relaxation of an Inverted Uterus", Am.J. Obest. Gynecol, vol. 166 4:1237–1238 (1992).

Peng, A.T.C., et al., "Intravenous Nitroglycerin for Uterine Relazation in the Postpartum Pateient with Retained Placenta", Anests., vol. 71 1:172–173 (1989).

Christoph Lees, et al., Arrest of preterm labour and prolongation of gestation with glyceryl trinitrate, a nitric oxide donor, *The Lancet,* vol. 343, No. 8909, May 28, 1994, pp. 1325–1327.

Jeffrey S. Greenspoon, et al., Breech extraction facilitated by glyceryl trinitrate sublingual spray, *The Lancet,* vol. 338, No. 8759, Jul. 13, 1991, pp. 124–125.

Word, R.A., et al., "Effects of cGMP on $[Ca^{2+}]_i$, Myosin Light Chain Phosphorylation, and Contraction in Human Myometrium", *Am. J. Physiol.,* 260:c861–c867 (1991).

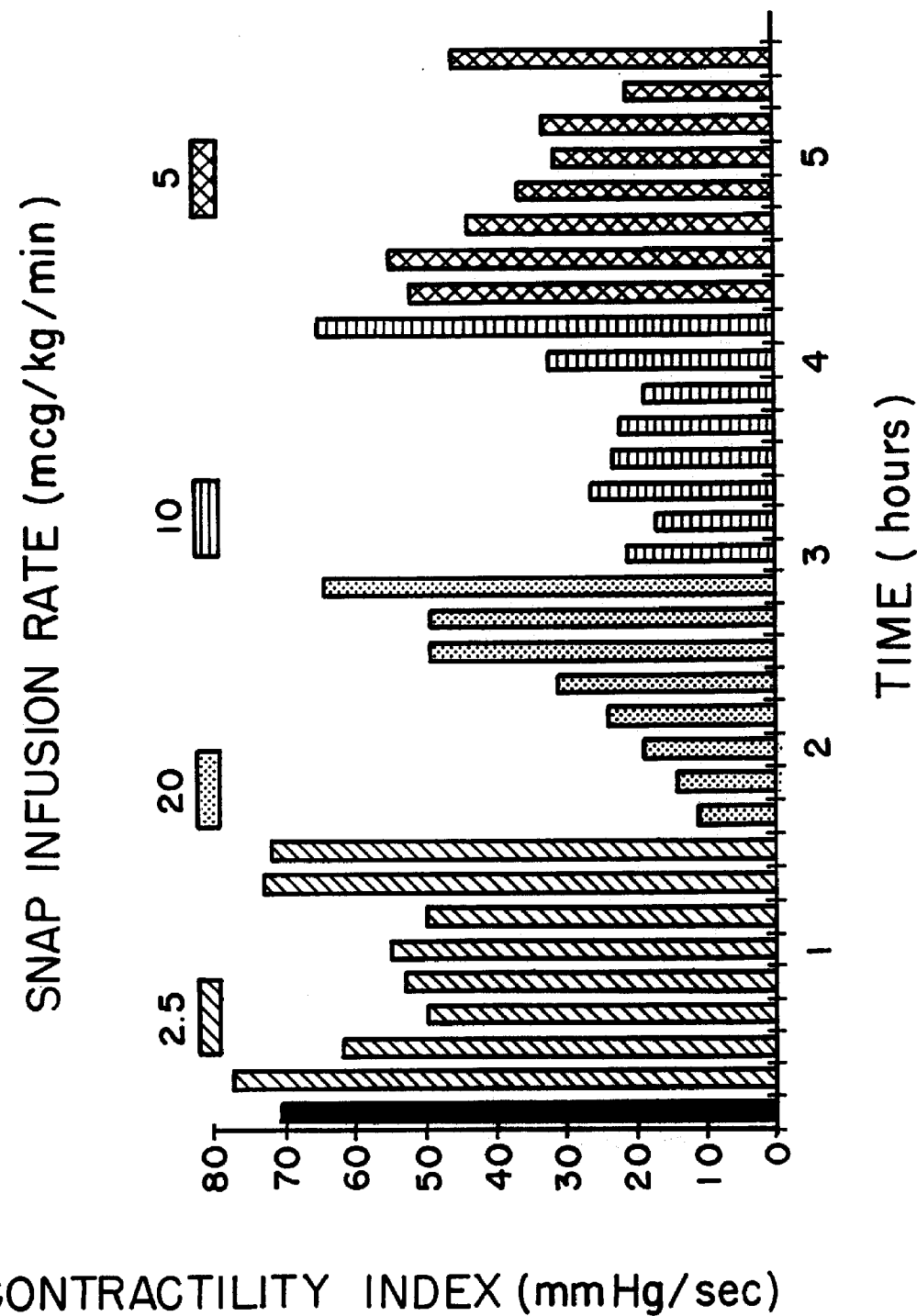

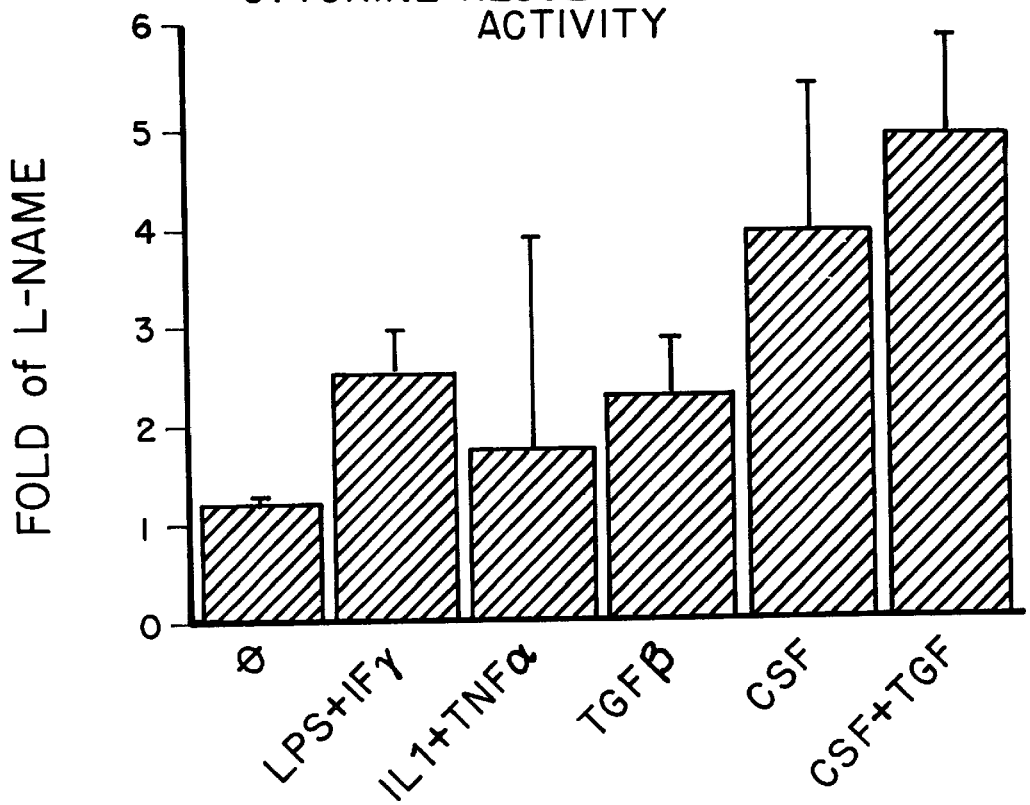
FIG. 17A CYTOKINE REGULATION of NOS ACTIVITY
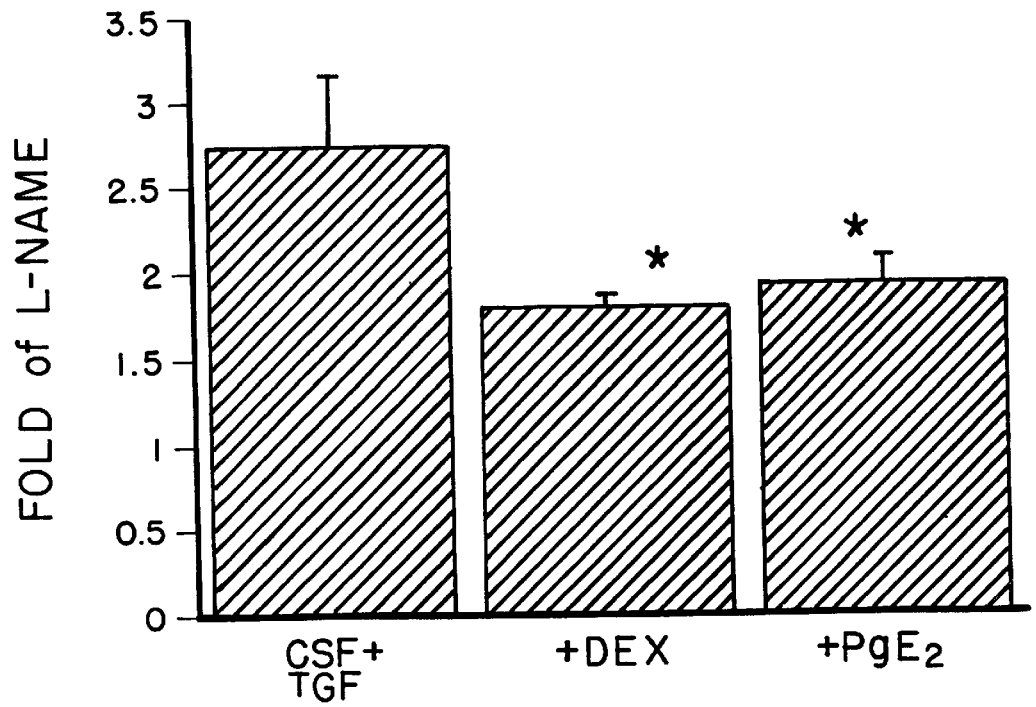
FIG. 17B

METHOD AND AGENTS FOR INDUCEMENT OF ENDOGENOUS NITRIC OXIDE SYNTHASE FOR CONTROL AND MANAGEMENT OF LABOR DURING PREGNANCY

This application is a continuation-in-part of the PCT application PCT/US95/02018, filed on Feb. 17, 1995, and a continuation-in-part of patent application Ser. No. 08/198,512, filed on Feb. 18, 1994, now U.S. Pat. No. 5,508,045, which is a continuation-in-part of patent application Ser. No. 07/959,006, filed on Oct. 9, 1992, (now abandoned).

This invention was made with government support under grant No. HD-26152, awarded by the National Institutes of Health. The government has certain rights in this invention.

BACKGROUND OF THE INVENTION

1. Field of the Invention

This invention concerns method and agents for endogenous control, treatment, management and prevention of preterm labor. In particular, the invention concerns the method for endogenous production of nitric oxide in myometrium directly by administering to a pregnant mammal an agent which induces production of nitric oxide or nitric oxide synthase or indirectly when the formation of nitric oxide is controlled through nitric oxide synthase gene transcription. Additionally, this invention concerns a non-invasive diagnostic procedure for detecting the presence and/or impending onset of premature labor.

2. Background and Related Disclosures

Spontaneous preterm labor during pregnancy remains an increasing problem confronting the medical community. Preterm labor, whether occurring spontaneously or the one which invariably follows any significant transuterine fetal manipulation such as needle puncture, fetoscopy, or hysterotomy for fetal surgery, presents a serious problem and is a limiting factor for all types of fetal intervention. The severe forms of spontaneous preterm labor or labor induced by an incision in the gravid uterus for open fetal surgery is resistant to all known forms of tocolysis. The management of preterm labor after fetal surgery is particularly difficult and dangerous for mother and fetus because aggressive treatment with magnesium sulfate, betamimetics and other hemodynamically-active tocolytic agents has resulted in sequelae for both mother and fetus.

Once preterm labor is diagnosed, the risks and benefits of labor inhibition must be weighed against those of allowing delivery to occur. The risks from labor inhibition are primarily related to the side effects of the labor inhibiting drugs. Once preterm labor is diagnosed and the gestational age is established as appropriate for labor inhibition, contraindications such as eclampsia, preeclampsia, ruptured placenta, dead or anomalous fetus, fetal distress or chorioamnionitis to premature delivery is determined and the particular available tocolytic agent is selected. Until now, tocolytic agents most often used to inhibit preterm labor are β-adrenoreceptor stimulants such as epinephrine or its synthetic analogs and derivatives salbutamol, terbutaline, isoxsuprine, ritodrine, and fenoterol, magnesium sulfate, prostaglandin inhibitors such as aspirin indomethacin and naproxen, ethanol and calcium channel-blocking agents such as nipedifine or nicardipine. However, the potential adverse effects and limited efficacy of these drugs limit their use.

Patients undergoing hysterotomy and fetal surgery typically experience difficulty with preterm labor despite treatment involving a regimen of preoperative indomethacin, intraoperative deep halogenated inhalation anesthesia, and postoperative administration of indocin, magnesium sulfate, and betamimetics. The majority of these patients has visible and palpable intraoperative uterine contractions often associated with fetal bradycardia from cord compression. These intraoperative contractions respond erratically to deepening anesthesia and to acute administration of magnesium sulfate or terbutaline. All the patients experience significant labor postoperatively. In mild form, such labor can be controlled by administration of intravenous tocolytics for few days. In severe form, it takes a week or longer to control postoperative labor with intravenous medication before oral or subcutaneous pump medication can be used. All patients undergoing hysterotomy eventually develop uncontrolled preterm labor, premature rupture of membranes, and premature delivery from 27–34 weeks gestation.

It is clear that even the best tocolytic regimen available currently is unsatisfactory for prevention or inhibition of preterm labor. Additionally to proving ineffective, such standard tocolytic regimen had potentially serious harmful effects on both mother and fetus. Halogenated inhalation anesthesia needed to achieve uterine relaxation had been shown to produce significant myocardial depression in both mother and fetus, the indomethacin produces constriction of the fetal ductus arteriosus, and serial echocardiograms in patients demonstrated that ductal constriction producing tricuspid regurgitation can lead to right-heart failure in the fetus. Additionally, indomethacin tocolysis has recently been shown to be associated with an increased risk of perinatal intracranial hemorrhage in the neonate, and the aggressive treatment of postoperative labor with maximal doses of magnesium and betamimetics seems to be quite toxic for the mother. It, therefore, appears that currently available tocolytic treatment has significant potential to harm the fetus.

Different pharmacological approaches using the above tocolytic drugs have been tried to control preterm labor. Recently, however, these drugs come under significant scrutiny concerning their effectivity and safety.

It would be therefore highly advantageous to provide a method and agents which would, in a rational and reproducible way, control, manage and inhibit preterm labor or, when applicable, induce labor in late pregnancies when such induction of labor is indicated.

Nitric oxide (NO) is a free radical with a very short half-life. Nitric oxide is synthesized from the amino acid L-arginine by the nitric oxide synthase (NOS). So far, the only clearly established role for nitric oxide is as a cytotoxic molecule for invading microorganisms and tumor cells. However, other physiological activity, such as acting as a neurotransmitter in the brain and in the periphery, affecting GI tract motility and penile erection were also observed. Nitric oxide is produced in vascular endothelial cells by the nitric oxide synthase and seems to mediate vascular smooth muscle relaxation by increasing levels of cGMP. Its effect on relaxation of intrapulmonary artery and vein was described in *J. Pharmacol. Exp. Ther.*, 228:33–42 (1984).

Nitric oxide, its physiology, pathophysiology and pharmacology is described in *Pharmacological Reviews*, 43:109–134 (1991). While there were some in vitro studies described in *Brit. J. Pharmacol.*, 34:604–612 (1968) concerning the effect of nitric oxide precursors on animal isolated uterus, such studies did not lead to any conclusion or advancement useful for control of labor, particularly preterm labor in human or mammal pregnancy.

The current invention provides a method and agents which enable clinicians to control, manipulate or inhibit preterm labor or induce labor in late pregnancies in safe and reproducible way. The method gives a clinician control over the labor progression until now unavailable, by administering to a pregnant woman nitric oxide source or inhibitors, alone or in a suitable combination with other agents and pharmaceutically acceptable excipients. Such treatment has not been heretofore available.

In alternative, the method of the invention provides means for therapeutic enhancement of the uterus capacity to make endogenous uterine nitric oxide, that is to induce endogenous tocolytic effect through the administration of hormones having a uterine-selective effect on inducing or up-regulating the expression of nitric oxide synthases in the myometrium or other agents selectively enhancing production of endogenous nitric oxide or inducing expression of nitric oxide synthase.

Finally, the method provides a non-invasive diagnostic tool for detecting the presence or impending onset of premature labor by monitoring the level of inducible nitric oxide synthase expression.

All patents and publications cited herein are hereby incorporated by reference in their entirety.

SUMMARY

One aspect of the current invention is a method for controlling and managing spontaneous or surgically induced preterm labor or for inducing labor in overterm pregnancy.

Another aspect of the current invention is a method for control, management and inhibition of preterm labor by manipulating levels of nitric oxide synthase.

Still another aspect of the current invention is a method for controlling and managing preterm labor or inducing labor in overterm pregnancy by administering to a pregnant woman compounds which alter nitric oxide availability.

Still yet another aspect of the current invention are agents which produce control or alter nitric oxide availability useful for control and inhibition of preterm labor or for induction of labor in overterm pregnancy.

Still another aspect of the current invention are therapeutic agents which are able to enhance endogenous tocolytic effect.

Still yet another aspect of the current invention are agents able to therapeutically enhance the capacity of the uterus to produce endogenous nitric oxide.

Still yet another aspect of the current invention is therapeutic induction of endogenous tocolytic effect by administration of hormones having a uterine-selective effect on induction of the expression of nitric oxide synthases in the myometrium.

Still yet another aspect of the current invention is a non-invasive diagnostic procedure for detecting the presence of impending onset of premature labor.

Yet another aspect of the current invention are pharmaceutical compositions comprising agents which produce, control or alter nitric oxide availability or manipulate the level of nitric oxide synthase, or which inhibit or slow down the breakdown of the substance in the muscle cells, guanosine 3':5'-cyclic monophosphate (cGMP), which is produced by the action of the nitric oxide and which is eventually responsible for the muscle relaxation, which compositions are useful for control of preterm labor or for induction of labor in overterm pregnancy and which compositions are administered to a pregnant woman alone or in combination with other pharmaceutically effective agents which potentiate nitric oxide action.

BRIEF DESCRIPTION OF FIGURES

The file of this patent contains at least one drawing executed in color. Copies of this patent with a color drawing will be provided by the Patent and Trademark Office upon request and payment of the necessary fee.

FIG. 2 is a dose response graph representing intrauterine pressure (IUP) and uterine electromyogram (EMG) of pregnant rhesus monkey experiencing preterm labor contractions in response to various doses of SNAP compared to a IUP and EMG response observed in control pregnant rhesus monkey having been given no medication.

FIG. 3 depicts the dose dependent effects of SNAP infusion on preterm labor in rhesus monkey.

FIG. 17 illustrates effects of cytokines on primary mouse uterine myocyte iNOS mRNA expression, myocytes treated with endotoxin, interferon, interleukin, tumor necrosis stimulating factors, macrophage colony stimulating factor or transforming growth factor a (FIG. 17A) and myocytes treated with dexamethasone or prostaglandin (FIG. 17B).

DEFINITIONS

Figure 1:
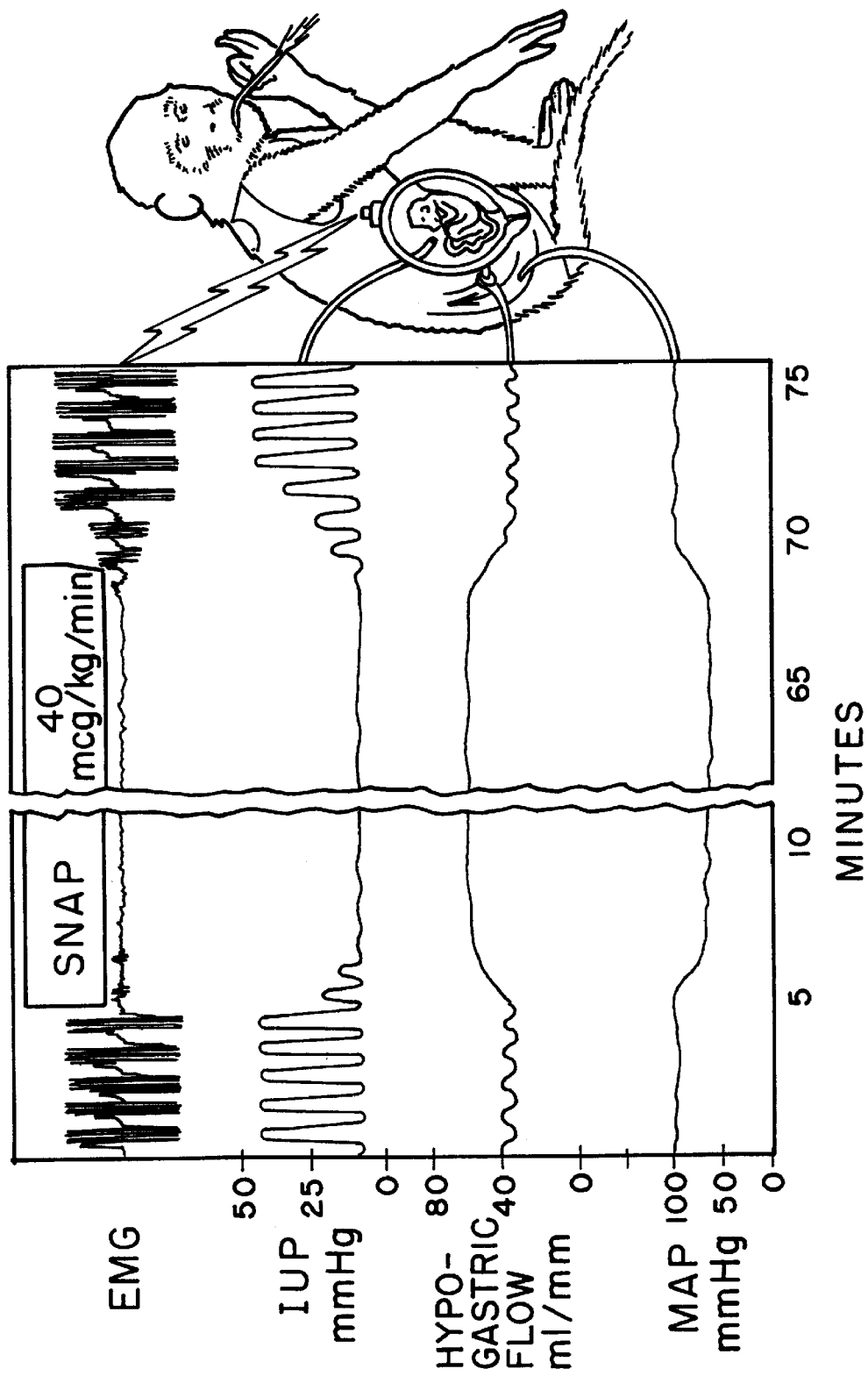
FIG. 1 is a schematic strip chart recording obtained from pregnant rhesus monkey demonstrating ablation of preterm labor after administration of nitric oxide donor S-nitroso-N-acetyl penicillamine (SNAP).
Figure 2A:
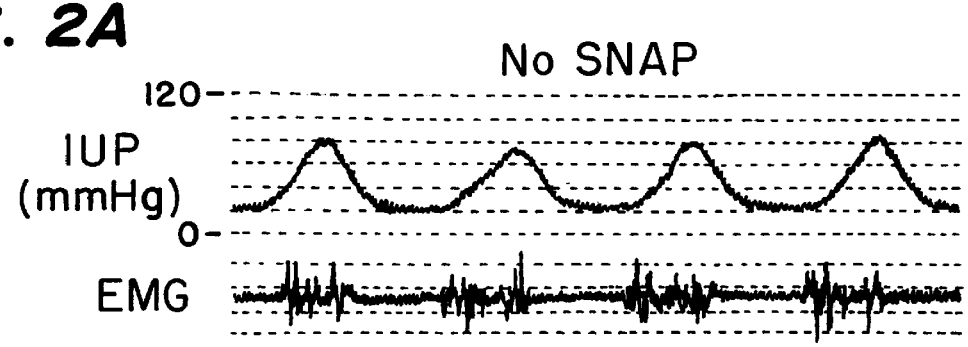
FIG. 2A shows IUP and EMG of untreated pregnant monkey.
Figure 2B:
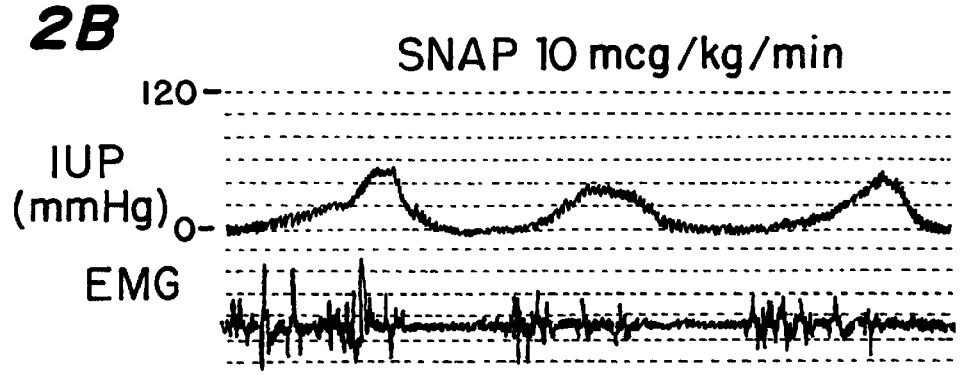
FIGS. 2B, 2C and 2D show IUP and EMG of pregnant monkey treated with SNAP 10, 20 and 40 mg/kg/min.
Figure 2C:
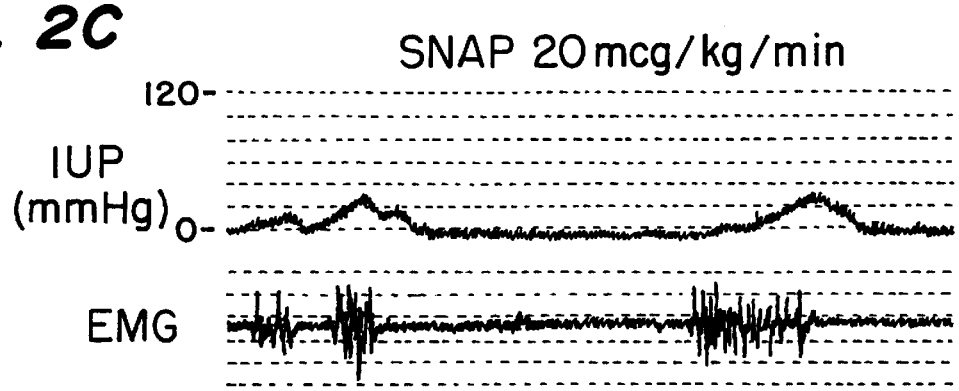
Figure 2D:
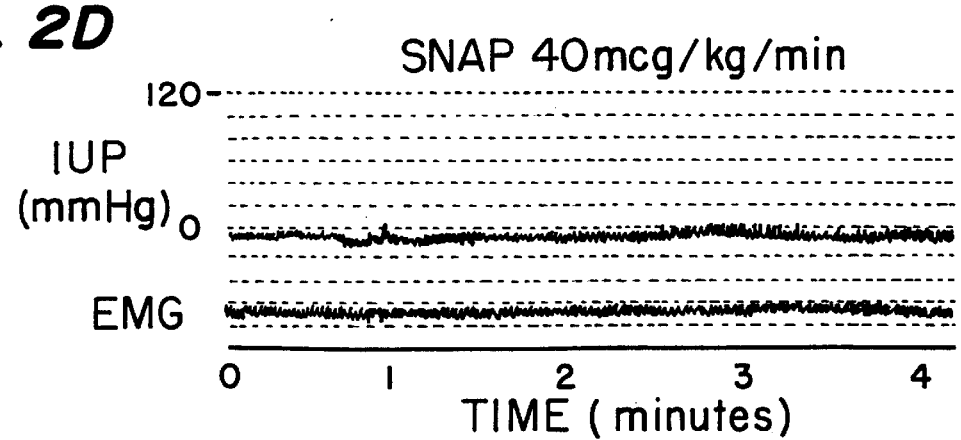

As used herein, the term:

"NO" means nitric oxide.

"NOS" means nitric oxide synthase.

"bNOS" means brain calcium sensitive nitric oxide synthase.

"eNOS" means endothelial calcium sensitive nitric oxide synthase.

"iNOS" means inducible calcium nonsensitive form of nitric oxide synthase originally identified in mouse macrophage cells.

"Nitric oxide source" means nitric oxide donor or precursor capable of potentiating the effect, or increasing the level of nitric oxide in utero and include but are not limited to S-nitroso-N-acetylpenicillamine (SNAP) and analogues thereof, nitric oxide nucleophiles or nitric oxide adducts such as diethylamino/nitric oxide (DEA/NO), DETA/NO or spermine or other nucleophilic groups known in the art, nitroglycerin and analogues thereof such as isosorbide dinitrate, nitropaste, nitropatches, nitroprusside and analogues thereof, other nitrovasodilators such as hydroxylamine, sodium azide, 2-isosorbide mononitrate, PETN, and analogues thereof, endogenous precursors of nitric oxide such as L-arginine, metabolic precursors of L-arginine.

"Nitric oxide synthase inhibitor" means a compound which is effectively able to prevent the nitric oxide synthase mediated production of nitric oxide from L-arginine, by competing with L-arginine as the substrate for the nitric oxide synthase and thus preventing nitric oxide production and include but are not limited to compounds such as $N^{\omega}$-nitro-L-arginine (N-NA), $N^{\omega}$-nitro-L-arginine methyl ester (L-NAME, $N^{\omega}$-mono-methyl-L-arginine (L-NMMA).

"Cytokines" means hormones which are soluble proteins released by cells which act non-enzymatically to regulate cellular function acting primarily in a local autocrine or paracrine regulatory function or serving as endocrine regulators. Exemplary cytokines are interferon gamma (Inf γ), interleukin-1 (IL-1β), interleukin-6 (IL-6), interleukin-8 (IL-8), tumor necrosis factor alpha (TNF-α), colony stimulating factor (CSF-1, GM-CSF) and transforming growth factor (TGF-β).

DETAILED DESCRIPTION OF THE INVENTION

This invention generally concerns a method and agents for control, management and manipulation of labor during pregnancy. The method is particularly useful for inhibition of spontaneous preterm labor which would, if untreated, result in premature delivery or abortion and for inhibition of surgically induced labor during transuterine fetal surgery. The method is also useful for inducing the labor in overterm pregnancies where the labor does not occur on term and when it is necessary to induce labor in order to assure the normal delivery.

This invention concerns a discovery that nitric oxide is a powerful mediator of uterine smooth muscle relaxation. Exogenously supplied nitric oxide was found to stop or ablate even well established preterm labor. The invention provides a way of regulating the levels of nitric oxide in utero by means of agents acting upon the nitric oxide or its enzyme nitric oxide synthase. Some of the present agents are useful to retard preterm labor, and others to induce labor leading to delivery or abortion.

The method of the invention provides means for therapeutic enhancement of the uterus capacity to produce endogenous uterine nitric oxide (NO), that is to induce endogenous tocolytic effect through the administration of hormones or other agents having an uterine-selective effect to induce nitric oxide synthases (NOS) in the myometrium.

Finally, the method provides a non-invasive diagnostic tool for detecting the presence or impending onset of premature labor by monitoring the level of iNOS expression.

I. Method for Exogenous Control, Treatment and Prevention of Preterm Labor

The present invention provides a novel method for control, treatment, management and prevention of preterm labor. The method comprises administering to a pregnant woman experiencing preterm labor before the 37 week of gestation, or to a mammal female experiencing preterm labor, a composition consisting essentially of a donor or a source of nitric oxide, alone or in combination with a uterine relaxant selected from the group consisting of agents capable of potentiating the effect, or increasing the level, of nitric oxide in utero in an amount effective to inhibit or counter the onset of uterine contractions. Such agents include but are not limited to nitric oxide donors such as for example, S-nitroso-N-acetylpenicillamine, nitric oxide nucleophiles and adducts, nitroglycerin, hydroxylamine, sodium azide, and diethylaminonitric oxide and other analogs thereof, and nitric oxide precursors such as L-arginine.

The methods for labor control were studied in vivo in rhesus monkey model specially developed for this purpose, and in vivo in sheep, in in vitro pregnant rat uterine tissue, in mouse uterine monocytes and also in controlled clinical settings. Results of all these studies provide evidence that the administration, preferably by intravenous infusion, of compound which is either a donor, source or a precursor of nitric oxide or inducer of endogenous tocolysis effectively suppresses the virulent uterine contractions appearing either spontaneously as preterm labor or which were induced by surgical manipulation of the uterus. Infusion of the nitric oxide donor or substrate suppressed and even ablated preterm labor or induced contractions. Administration of these agents induced changes in uterine contractility through levels of nitric oxide. Infusions of normal saline or other control agents had no effect either on contractility or on maternal hemodynamics.

In one embodiment, the current invention provides uterine relaxing composition comprising a nitric oxide donor capable of increasing or maintaining levels of nitric oxide in uterus and in this way controlling, inhibiting, managing and regulating preterm labor.

II. Method for Endogenous Control, Treatment and Prevention of Preterm Labor

In alternative, the present invention provides a method for endogenous control, treatment, management and prevention of preterm labor.

The method comprises induction of endogenous production of NO in myometrium and prevention of the initiation of preterm labor. Such endogenous tocolysis may be induced directly by administration systemically, locally or in any other conventional drug delivery way the agent which induces production of NO or NOS, or indirectly when the formation of NO is controlled through NOS gene transcription.

Endogenous control, treatment and prevention is based on findings that certain hormones of which production in uterus is increased during pregnancy are capable of increasing the expression of the gene which controls production and activity of iNOS isoform. The capacity of the uterus to produce NO endogenously is therapeutically enhanced by the administration of the hormones having a uterine-selective effect on iNOS in the myometrium. Administration of such hormones constitute endogenous tocolytic effect.

The augmentation of uterine NO production is achieved by administration of agents enhancing the capacity of the uterus to make endogenous uterine NO. Such endogenous uterine NO production constituting endogenous tocolytic effect is achieved through administration of agents having a uterine-selective effect on iNOS in the myometrium. Such agents include systemically or by any other conventional route administered cytokines, growth factors, or sense or antisense oligonucleotides. Exemplary cytokines are Inf $\gamma$, IL-1$\beta$, IL-6, IL-8, TNF-$\alpha$, CSF-1, GM-CSF and TGF-$\beta$. Exemplary growth factors are epidermal growth factor (EGF), fibroblast growth factors (FGFs), eicosanoids, alone or in combination with hormones such as progesterone or estradiol 17$\beta$, of which the levels are very high in pregnancy acting as an adjuvant. Exemplary sense or antisense oligonucleotides are antisense oligonucleotides directed against iNOS gene promoter repressor elements, or sense oligonucleotides directed towards iNOS gene promoter or promoters of genes for iNOS gene transcriptional regulators, which selectively increase uterine NO production. These agents are also delivered to the uterus in a targeted manner, for example, by complexing these agents with other biomolecules, such as hormones, antibodies, or nutrients, which are selectively taken up by or concentrated within the uterus or myometrium. Specific examples of these targeting techniques are complexing an agent with an oxytocin receptor antagonist, complexing an agent with an antibody directed to a uterine-specific antigen, and using liposomal carriers to deliver agents.

Additionally, agents are administered which act indirectly on NO production augmentation. These agents are putative control elements which modify the expression of transcriptional regulatory proteins such as nuclear factor NF Kappa B Jun/fos, tumor necrosis factor (TNT-$\alpha$), NF-1l6, activator protein (AP-1), octamer binding protein, (OCT-1), (OCT-2), PU-1, and gamma activation factor (GAF), which in turn alter gene expression in a manner which increases uterine NO production.

Any and all agents named in sections I and II are conveniently administered systemically or locally to the uterus via the peritoneal cavity or the vagina/cervix.

III. Diagnostic Monitoring of iNOS levels

The third aspect of the invention is method for diagnostic monitoring of levels of iNOS expression by the uterus or by the myometrium. This method provides a non-invasive diagnostic mechanism for detecting the presence, the extent, or risk of impending onset of premature labor.

The diagnostic monitoring includes but is not limited to monitoring levels of key regulatory molecules present in blood, saliva, urine or other body fluids, or monitoring levels of NO and its chemical precursors, cofactors, metabolites, cytokines or hormones.

IV. Method for Induction and Augmentation of Uterine Contractions

The present invention additionally provides a method for the induction and augmentation of uterine contractions. By decreasing the levels of nitric oxide or by administering nitric oxide inhibitors, uterine contractions can be effectively induced.

Thus, in another embodiment, the present invention provides a uterine contracting composition, comprising an uterine contracting agent capable of countering the effect, or reducing the level of nitric oxide, and optionally a second agent selected from the group consisting of other antigestational agents, anesthetics, analgesics, and mixtures thereof.

This method can be effectively used to induce labor and contraction in overterm pregnancies when the labor induction is indicated. In such a case, nitric oxide level is decreased by administration of nitric oxide inhibitors alone or in combination with other agents.

V. In Vivo Studies

The role of nitric oxide in control of labor and contractions was studied in a clinically relevant monkey and sheep models.

One of the primary limitations of research on preterm labor is the absence of a suitable experimental model. Up to the present time, the unpredictable nature of preterm labor in humans and animals had made its systematic study difficult. For the purposes of this invention, the non-human primate animal models similar to the human system, and the sheep model were developed. Experimental tests performed in primates and in other high mammals, permitted a simple extrapolation of the invention utility, applications and regimes to humans.

Both the primate and sheep models were used to study the mechanism by which nitric oxide mediates uterine relaxation, the role of endogenous nitric oxide production in pregnancy, the role of exogenously administered drugs that increase the level of nitric oxide, as well as their combination with other agents to determine their efficacy in the treatment of preterm labor, the timing and route of administration for clinical use, and adverse or long-term effects of these drugs on the mother, fetus or neonate.

One form of induction of preterm labor, which was observed in over 400 fetal surgical procedures in non-human primates is labor induced by hysterotomy, an incision of the uterus. In monkeys, as in humans, mid- to late-gestational hysterotomy reliably induces labor. This labor occurs 100% of the time, it is difficult to control with standard tocolytic regimens, and has a predictable course lasting 5–7 days. Hysterotomy induced preterm human labor corresponds to spontaneously occurring preterm labor, and therefore, provides a unique opportunity to study labor. When combined with sensitive methods to detect, monitor, and quantitate preterm labor, the monkey hysterotomy model provides a reproducible model which is representative of post-hysterotomy preterm labor in humans.

Because of its smooth muscle relaxation activity observed before in other tissues, nitric oxide was studied for its mediating activity in uterine smooth muscle relaxation on the primate model having induced preterm labor by hysterotomy.

Eleven time-mated pregnant rhesus monkeys (*Macaca mulatta*), having gestational age from 106 to 137 days, and expected term at 165 days were equipped and accustomed to a vest suitable to be worn in awake state and to cover and protect various sensors, tubings, catheters and probes implanted into the monkey uterus. The schematic chart of implanted sensors and probes is shown in FIG. 1 which also illustrates the ability to continuously monitor the uterine muscular activity and contractions by electromyograph (EMG), intrauterine pressure (IUP), hypogastric flow and maternal mean arterial pressure (MAP).

Prior to initiation of studies, monkeys were premedicated with atropine 0.02 mg/kg and ketamine 10 mg/kg given by intramuscular injection (IM) and anesthetized with 1.5% isofluorane for placement of monitoring catheters, flow probes, and radiotelemeter for electromyogram. Polyvinyl fluid-filled catheters for pressure transduction were placed in the maternal common femoral artery and vein, the hypogastric artery, and the intraamniotic activity. An ultrasonic flow probe was placed around the left hypogastric artery to measure uterine blood flow. A polyvinyl catheter in the common femoral vein was used for infusions. All catheters were tunneled subcutaneously to the back where they exited into a vest and steel tether system. A radiotelemeter with two electrodes placed 1 cm apart on the uterine fundus and a fluid-filled pressure catheter placed through the myometrium into the amniotic space continuously transmitted the uterine electromyogram (EMG) and the intrauterine pressure (IUP). All data were continuously displayed and stored on a strip chart recorder. Postoperatively, when the monkeys recovered they were returned to their cages so they could be studied in a chronic, awake state. The monkeys received oxymorphone 0.15 mg/kg IM every 8 hours and cephalexin 15 mg/kg by intravenous infusion twice daily. Monkeys were handled in accordance with a protocol approved by the Committee on Animal Research. Detailed protocol of the monkey model is described in Example 1.

In these studies, it was observed that maternal laparotomy and uterine manipulation for placement of monitors and catheters consistently initiated uterine irritability which, in all monkeys, progressed to organized labor over several days, usually worse at night. When no tocolytic therapy was given, labor progressed until membrane ruptured and the fetus was delivered. As labor progressed, the uterine EMG tracings evolved from diffuse random spikes associated with small increases in intrauterine pressure into organized, fusiform shaped complexes associated with high-amplitude pressure increases. As expected, uterine blood flow decreased during contraction resulting in increased maternal arterial pressure.

Typically, the vested monkey had surgically induced preterm labor according to Example 1 and was then treated with compounds that alter nitric oxide availability.

In four monkeys, nitric oxide source was administered by intravenous infusion of S-nitroso-N-acetylpenicillamine (SNAP) dissolved in 0.9% saline (0.2 mg/ml). SNAP infusion rate (range 0.625 µg/kg/min to 40 µg/kg/min) was titrated in all monkeys to maintain maternal mean arterial blood pressure (MAP) above 60 mmHg.

FIG. 1 illustrates EMG, IUP, hypogastric flow and MAP values in one monkey experiencing severe preterm labor contractions. During the preterm labor episode, observed IUP was between 5 to about 40 mmHg and regular muscular contractions appearing in regular intervals were observed as seen on EMG portion of the chart. During the contractions, hypogastric flow oscillated around and generally was lower than 40 ml/mm. Maternal arterial pressure (MAP) increased to about 100 mmHg from the normal pressure around 60 mmHg. Administration of SNAP in concentration 40 µg/kg/min resulted in almost immediate inhibition of muscular contractions as well as in decrease of intrauterine pressure to a normal level around 5–7 mmHg. Hypogastric flow increased to about 50–60 ml/min and maternal arterial pressure decreased to close to normal levels of around 50–60 mmHg. These parameters were held constant and labor held in abeyance for the entire period when the infusion of SNAP repeatedly was administered. When the infusion of SNAP was ended around 68 minutes, the EMG, IUP, MAP and hypogastric flow levels returned to its pretreatment levels and preterm contractions returned with the same frequency and strength. These results have been observed in all treated monkeys. The strength of contractions, expressed as uterine contractility index, before and after the SNAP infusion were dose dependent. Results obtained after administering various doses are shown in Table 1.

TABLE 1

Uterine Contractility in Rhesus Monkey

| MONKEY # | GESTATIONAL AGE | SNAP DOSE (µg/kg/min) | INDEX before | INDEX after | % CHANGE | OUTCOME |
|---|---|---|---|---|---|---|
| 1 | 112 d | 10 | 43 | 13 | 70 | Sacrificed |
|   |       | 10 | 49 | 4  | 92 |            |
|   |       | 10 | 80 | 19 | 76 |            |
|   |       | 10 | 82 | 31 | 62 |            |
| 2 | 111 d | 5  | 49 | 29 | 41 | Sacrificed |
|   |       | 10 | 95 | 53 | 44 |            |
|   |       | 20 | 84 | 31 | 63 |            |
|   |       | 40 | 39 | 1  | 97 |            |
| 3 | 128 d | 0.625 | 44 | 17 | 64 | Sacrificed |
|   |       | 1.25  | 59 | 18 | 70 |            |
|   |       | 2.5   | 53 | 10 | 82 |            |
| 4 | 137 d | 2.5 | 73 | 51 | 31 |            |
|   |       | 5   | 55 | 30 | 46 |            |
|   |       | 10  | 62 | 20 | 68 |            |
|   |       | 20  | 71 | 14 | 80 |            |
|   |       | 20  | 90 | 50 | 45 |            |
|   |       | 40  | 90 | 20 | 78 |            |
| 5 | 139 d | None | 4 | 105 |  | Labor increased abort after 28 h |
| 6 | 111 d | None | 8 | 119 |  | Labor increased abort after 32 h |

Normal term in monkey is 165 days.

Five monkeys having induced labor by hysterotomy at gestational age as given in Table 1 were treated either repeatedly with one dose (monkey 1) where the dose of 10 µg/kg/min was repeatedly administered to monkey in labor, or with various doses (monkeys 2–4). Index before and after the treatment was determined and expressed as % of change against untreated (before) state. The monkey was first treated, then left without treatment for 30 minutes and then the treatment with the same or different dose was repeated. As seen in Table 1, each treatment of monkey 1 resulted in decrease in contractions from 62–92%. In monkeys 2–4, treated with various increasing doses of SNAP, decrease in contractions was dose dependent and varied from 31 to 97%, depending in the dose and also on the degree of contractions before the treatment was initiated.

To quantify labor, a uterine contractility index derived by integrating the area under the intrauterine pressure curve in 10 minute intervals was developed. Dose response to SNAP was determined in monkeys by calculating the percentage change in the uterine contractility index (the difference between the average contractility index during the 30 minutes of infusion and the average contractility index during the 30 minutes period immediately preceding the SNAP infusion), for varying dose of SNAP.

Table 1 also shows that in 2 untreated monkeys, preterm labor continued to abortion at 28 or 32 hours later. In treated animals, 31–97% dose dependent change in uterine contractility was observed.

In addition to SNAP, 8-bromoguanosine 3':5'-cyclic monophosphate, given as an intravenous 5-mg/kg bolus to two monkeys, showed only transient effect on contractions. Zaprinast given as an intravenous 3 mg/kg bolus to two additional monkeys, decreased contractions by about 35%.

At any time in the progression from uterine quiescence to full labor, infusion of SNAP or any other tested compound ablated the EMG and mechanical activity of the contracting uterus. FIG. 1 depicts the response to SNAP infusion on continuously recorded uterine EMG, intrauterine pressure, maternal mean arterial pressure (MAP), and hypogastric artery blood flow. The response depicted in FIG. 1 was typical and very consistent for all tested monkeys. In four monkeys, infusion of SNAP for 30 minutes (17 occasions) was always associated with a decrease in the frequency and amplitude of contractions (Table 1).

The effects of SNAP on uterine contractions were dose dependent. As SNAP infusion increased, contractions decreased in amplitude and frequency and were ultimately obliterated as seen in FIG. 2. FIG. 2 shows the dose dependency of monkey uterus contractility in a monkey experiencing severe contractions (FIG. 2A) having subsequently administered 10 (FIG. 2B), 20 (FIG. 2C), and 40 (FIG. 2D) μg/kg/min of SNAP by infusion. Control monkey received no SNAP but was injected with the same volume of saline. The uterine contractility index, which considers both amplitude and frequency of contractions, decreased with increasing doses of SNAP and ultimately prevented preterm delivery which occurred in untreated control.

As seen from FIG. 2, SNAP in 40 μg/kg/min dose was sufficient to almost completely abate the preterm labor while the SNAP dose of 20 μg/kg/min decreased the number and strength of contractions by about 75%. The lower dose 10 μg/kg/min decreased contractions by about 30%, slowing the frequency and decreasing the strength of contractions.

FIG. 3 confirms the ability of nitric oxide to inhibit or decrease contractions in dose dependent manner. In FIG. 3, one monkey experiencing contractions following hysterotomy was treated with different individual doses of SNAP over 30-minute intervals. Doses were assigned in random order. The SNAP infusion was stopped for at least 30 minutes between doses to allow the contractility index to recover. The time of actual infusion is shown as a bar with dose shown above.

The effects of SNAP infusion on preterm labor in the monkey were dose dependent. The uterine contractility index was derived by integrating the area under the intrauterine pressure curve in each ten-minute interval. The bar graph shows that infusing different doses of SNAP over 30-minute intervals in monkey depressed the uterine contractility index in a dose-dependent manner.

While even the lowest dose of 2.5 μg/kg/min of SNAP infusion was able to decrease contraction by about 30%, both 10 and 20 μg/kg/min doses were able to substantially decrease the contractility. Both 20 and 10 μg/kg/min doses of SNAP infusion for 30 minutes was able to decrease contraction during the infusion but also for another 30 minutes following the infusion.

Figure 4:
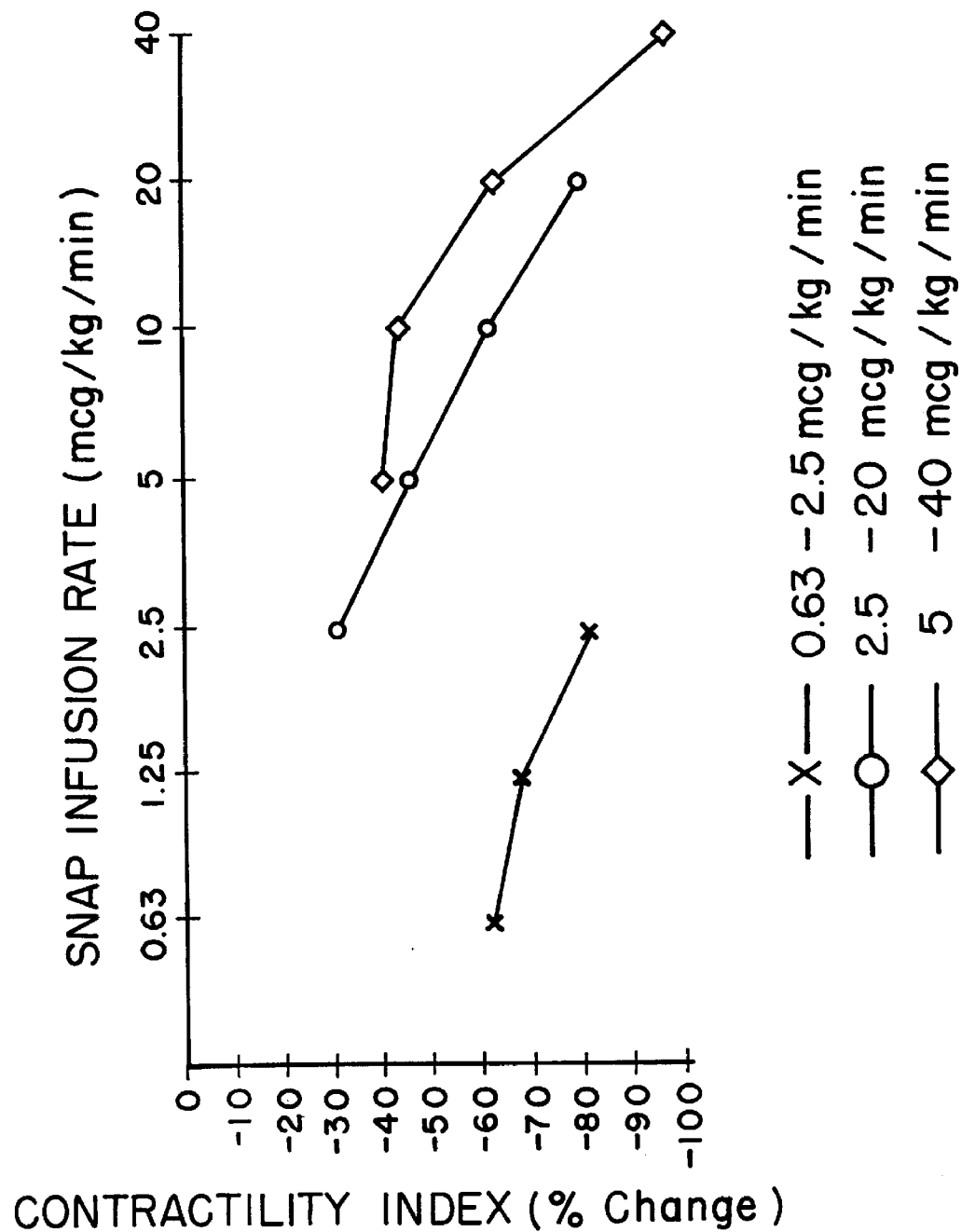
FIG. 4 depicts dose response curves expressed in % of change in contractility index observed in three rhesus monkeys.

FIG. 4 illustrates dose dependent response of the contractions in three monkeys. The curves were obtained by determination of % change of contractility index following the administration of various doses of SNAP. FIG. 4 illustrates dose response to administration of SNAP. As can be seen, the infusion rate from 0.63 to 2.5 μg/kg/min elicited the smallest response. The infusion rate from 2.5 to 20 μg/kg/min elicited about 50% decrease in uterine contractility index while the infusion rate from 5–40 μg/kg/min elicited the greatest response. Each studied monkey had a different sensitivity to SNAP, probably reflecting the stage of preterm labor, but they all responded with a dose-dependent decrease in uterine activity.

The vasodilatory effect of SNAP infusion on preterm labor, that is the decrease in mean arterial pressure and increase in blood flow to the uterus, were all dose dependent. There was no significant difference between SNAP infused into the systemic circulation via the femoral vein compared with similar doses infused directly into the uterine circulation via the hypogastric artery.

In vivo studies in monkey model confirmed that nitric oxide donor SNAP was able to suppress the virulent uterine contractions induced by surgical manipulation of the uterus. Infusion of SNAP suppressed and even ablated those contractions in dose dependent manner. These studies confirmed that SNAP-induced changes in uterine contractility and maternal hemodynamics were due to mediation through nitric oxide, since infusion of normal saline or N-acetylpenicillamine (SNAP precursor) dissolved in dimethyl sulfoxide had no effect on the uterine contractility index or maternal hemodynamics.

The observation that exogenous nitric oxide inhibits postoperative preterm labor in the rhesus monkey In vivo provides new evidence of the mechanism of uterine smooth muscle contraction affected by the administration of nitric oxide source. Nitric oxide is known to relax vascular smooth muscle by activating guanylate cyclase and increasing cytosolic levels of guanosine 3':5'-cyclic monophosphate (cGMP). It would therefore be expected that compounds which increase cGMP levels would effect uterine contractility. In these monkey studies, nitroprusside increased cGMP levels but had no effect on spontaneous contractions. Attempts to provide cGMP directly by injecting 8-bromo-cGMP (5 mg/kg), a cGMP analogue, produced only transient reductions in uterine contractions in two monkeys. Attempts to raise levels of endogenous cGMP with Zaprinast, a cGMP-selective phosphodiesterase inhibitor described in *Biochem. Pharmacol.*, 38:9–15 (1989) decreased the uterine contractility index by 35% in two monkeys. It is therefore clear that the nitric oxide activity on preterm labor contractions does not depend on whether the donor compound raises endogenous levels of cGMP or not.

Other nitrovasodilators, including nitroglycerin, hydroxylamine, and sodium azide, were also studied. Nitroglycerin 2 mg/kg/min infused into the chronic vested monkey, using model described in Example 1, had very little effect on either uterine contractility or maternal hemodynamics, suggesting the rhesus monkey lacks the specific tissue sulfhydryl groups necessary to form the S-nitrosothiol reactive intermediate that spontaneously releases nitric oxide. On the other hand, both in sheep with spontaneous labor contractions and in human patients undergoing hysterotomy for fetal surgery, as seen in Example 7, intravenous nitroglycerin given intraoperatively provided immediate relaxation of the contracted uterus and, given postoperatively, suppresses preterm labor. Thus, there seems to be a species difference in nitric oxide donors' effect on preterm labor contractions.

This finding confirms the utility of nitric oxide as effective tocolytic in humans. Human patients respond to SNAP and nitroglycerin while monkeys were shown to respond to SNAP and other nitric oxide donors but not to nitroglycerin.

One potential advantage of nitric oxide as a tocolytic agent is that it appears to increase blood flow to the uterus without at the same time effecting the fetus circulation. In current monkey studies, as expected, infusion of exogenous nitric oxide donor SNAP produced a dose-dependent vasodilation reflected in decreased maternal mean arterial pressure (MAP) and increased blood flow through the hypogastric artery to the uterus. The dramatic effect of exogenous nitric oxide in ablating uterine contractions suggests that endogenous nitric oxide may be responsible for maintaining uterine relaxation during pregnancy.

Effect of substrate for nitric oxide synthase, on preterm labor inhibition was also studied. Neither the administration of substrate, L-arginine to the contracting uterus, nor infusion of nitric oxide synthase inhibitors into the quiescent uterus were able to change the uterine contractility index. This suggested that nitric oxide availability in the intact pregnant monkey was not substrate dependent and sensitive. However, these compounds were observed to have an effect in human patients and in other species.

In vivo studies were further performed in sheep, using procedure of Example 5. Pregnant sheep were intravenously injected with nitroglycerin in doses from 1–3 $\mu$g/kg/min. These doses immediately abolished preterm contractions observed before. This further confirms that the effect of individual nitric oxide donors, substrates and NOS inhibitors is species dependent and cannot be predicted without extensive experimental determination of efficacy of each individual compound in each species, including humans.

In vivo studies performed in support of this invention determined that continuous production and availability of endogenous nitric oxide is responsible for uterine relaxation during pregnancy and that lack, decreased level or withdrawal of nitric oxide during pregnancy induces labor or parturition which is reversible upon administration of exogenous donor of nitric oxide in sufficient amount. Both the identity of the donor and the quantity of the exogenous nitric oxide donor are species dependent and must be individually determined.

Nitric oxide was conclusively shown to play a role in labor during pregnancy. Lack of nitric oxide results in preterm labor and can lead to premature delivery. The preterm labor is effectively countered by the method of current invention which provides to a pregnant woman or mammal suffering from preterm labor a sufficient amount of exogenous nitric oxide source compound able to inhibit preterm labor contractions and to allow continuation of normal pregnancy to term.

VI. In Vitro Studies

Current invention is further supported by in vitro studies on rat pregnant uterus or mice myocytes. In these studies, NOS activity was demonstrated to be present in nerves, blood vessels and decidua of gravid rat uterus by the NADPH-diaphorase staining method and by other methods. NOS activity was quantitated in subcellular fractions of pregnant, laboring and post partum rat uterus. Results of these in vitro studies further confirm that NOS is present in multiple structures within the uterus. Its presence in two cellular compartments also suggests that more than one form of NOS is present in the uterus and that the uterine NOS may be different from other known types of NOS.

Reduction in NOS activity at parturition shows that nitric oxide contributes to the maintenance of uterine contractile quiescence during gestation. Uterine tissue fixed during labor demonstrated markedly less NOS. Quantitation NOS activity in subcellular fractions of pregnant and laboring uterus revealed its presence in both the cytosolic and the membranous compartments of uterine homogenates. In both cellular subfractions the enzyme activity decreased significantly from pregnancy to term.

All these findings support the current invention which concerns a method for treatment, management, inhibition and control of preterm labor by administration of nitric oxide donor, or substrate in sufficient amount to exogenously supply endogenously missing or reduced nitric oxide.

For in vitro studies, isolated uterine tissue obtained from time-mated pregnant rats used according to procedure described in Example 2. Additionally, some studies were performed on mouse uterine myocytes.

1. Studies of Nitric Oxide Synthase

To determine whether nitric oxide donors can be converted to nitric oxide, levels of nitric oxide synthase were determined.

Nitric oxide synthase is the enzyme which converts nitric oxide substrate (L-arginine) to nitric oxide. The existence of up to six isoforms of the NOS enzyme are known from protein isolation studies. These forms differ primarily in their presence in either cytosolic or microsomal subfractions of tissues, their sensitivity to $Ca^{++}$/calmodulin, and by the inducement of their activity by a variety of factors and cytokines.

The presence of NOS in a tissue may be demonstrated histochemically with NADPH diaphorase reaction by its ability to reduce the nitro-blue-tetrazolium dye to a blue-black formazan. The reaction is NADPH-dependent. The diaphorase reduction has been demonstrated biochemically and immunohistochemically using antibody to NOS which were previously shown to co-localize with the formazan from NOS in the central and peripheral nervous system.

The results of the present studies are consistent with prior observation of diaphorase staining in uterine nerves in the myometrium, endometrium, along uterine blood vessels and decidual endometrium. Such nerve staining was observed to be much more prominent in the pregnant than in the non-pregnant uterus.

Nitric Oxide Synthase Localization in Decidua, Vascular Endothelium, and Myometrial Nerve Plexus To determine whether uterus possesses cellular mechanism for production of nitric oxide, the presence of NOS in decidua, vascular endothelium and myometrial nerve plexus was studied.

Full-thickness sections of virgin, pregnant, and post-partum rat and monkey uterus were stained via a modification of the NADPH-diaphorase staining method described in *Society of Neuroscience Abstracts,* 11:1201(1986).

Uterine samples were taken from 15–17 days gravid animals. NOS was localized within the intramural nerve fibers and the endothelium lining spiral arterioles within layers of the myometrium of the uterus.

The intensity and number of NOS positive nerve fibers was found to be greater in the gravid uterus than that in the virgin uterus and in the post-partum uterus. Staining of the gravid decidua produced the intense staining of the glandular epithelial cells whereas the glandular cells of the endometrium in non-pregnant uterus were only mildly stained. A post-term rat uterus where delivery occurred 12 hrs prior to sampling, showed only minimal staining of the decidual remnant and lesser staining of nerve fibers evidencing decreased NOS activity.

Characterization of NOS Enzyme in Rat Uterus

In order to determine the NOS function in pregnancy and preterm labor, its specificity with respect to its localization was studied by determining the co-factor requirements of the NOS enzyme in crude uterine subfractions.

The crude uterine subfractions were prepared by differential centrifugation. The NOS activity was determined using the $^3$H-arginine to $^3$H-citrulline conversion assay according to *Biochem. Biophys. Res. Comm.*, 185: 960 (1992).

Two distinct types of NOS activity were found in the full-thickness of uterine tissue samples. A first activity was found to be present in a particulate, membrane bound fraction (30 kg pellet). This activity was not stimulated by calcium/calmodulin (specific activity ca 1.89 pmol/mg protein/min). The second activity was found in the soluble fraction (30k×g supernatant) (specific activity ca 1.64 pmol/mg protein/min). This activity significantly increases in the presence of calcium and calmodulin (CaCM).

These results show that at least two different forms of the enzyme are present in uterus: a putative membranous form which is $Ca^{++}$-insensitive and a potentially cytosolic form which can be stimulated by $Ca^{++}$. These two enzymes seem to be different from the presently characterized NOS gene products which are known to be cytosolic $Ca^{++}$-sensitive (neuronal), cytosolic $Ca^{++}$-nonsensitive (macrophage), or a $CA^{++}$-sensitive membranous form (endothelial).

The particulate activity of the NOS found in uterus was shown to be different from the above three forms. These results suggest that potentially novel, until now unknown forms, of NOS are additionally present in the uterus.

Comparison of NOS Activity in Pregnant, of Actively Laboring and in Post Partum Rat Uterus In order to confirm the function of NOS during pregnancy and its involvement in active labor, NOS activity in subcellular fractions of actively laboring rat uterus was compared to a post partum rat uterus.

Figure 5:
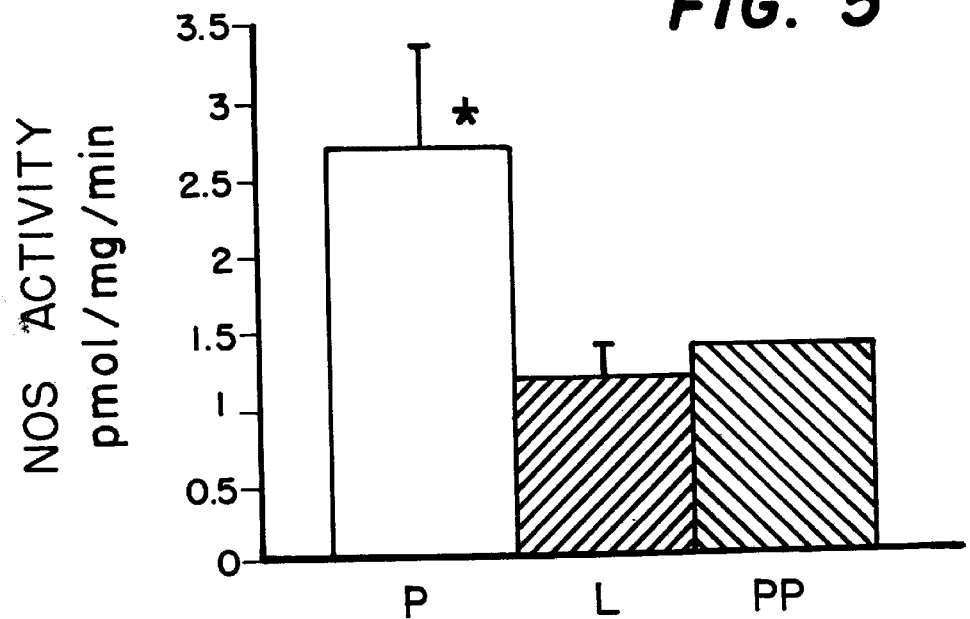
FIG. 5 depicts total nitric oxide synthase (NOS) activity in pregnant, laboring and post partum rat uterus.

An increase in NOS activity was found during pregnancy (P) when compared with the NOS activity during active labor (AL) and with post partum (PP) activity (FIG. 5). This difference was significant in all subfractions of the enzyme (p=0.021–0.028). NOS enzyme activity was present in both crude soluble and membranous subfractions of uterine homogenates. The production of [$^3$H]-citrulline was linear with time for up to 60 minutes. $^3$H citrulline production was dependent upon NADPH, an essential cofactor for NOS.

Total NOS enzyme seen in FIG. 5 was highest at 2.7 pmols/mg/min±0.68 in the preterm (P) 16 day pregnant uterus and declined significantly to 1.18 pmols/mg/min±0.22 in term laboring tissue (L) or in post partum tissue (PP) to 1.4 pmols/mg/min±0.13. In both subfractions, NOS activity could be increased by addition of calcium and calmodulin.

Figure 6:
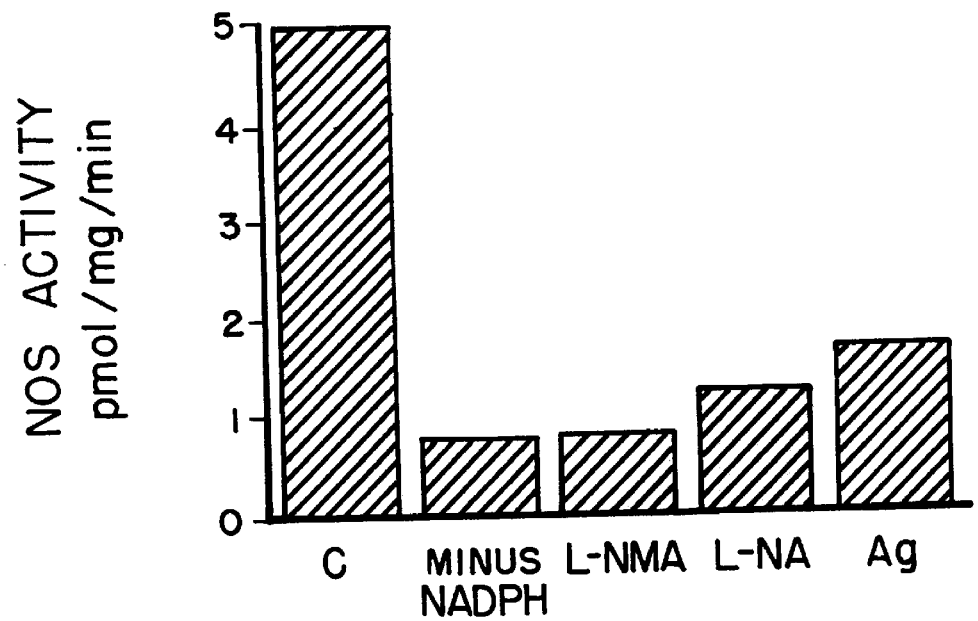
FIG. 6 depicts response of NOS activity to various NOS inhibitors.

When the NOS activity was inhibited with L-arginine analogs, enzyme activity seen in FIG. 6 in the presence of L-nitro-methylarginine (L-NMA, 0.5 mM) was less than 20% of the total uninhibited NOS activity and in the presence of L-nitroarginine (L-NA, 0.5 mM), the NOS activity was 26% of total NOS activity. Aminoguanidine (AG, 1 mM) inhibited 34% of total NOS activity.

Ultracentrifugation of the post-mitochondrial supernatant fraction to resolve cytoplasmic and microsomal uterine subfractions verified that NOS activities measured in the more crude subfractions consisted of both cytoplasmic as well as microsomal membranous isoforms of NOS.

These data show that the increase in NOS activity leading to the endogenous production of nitric oxide during pregnancy occurs in a manner consistent with a role in maintaining uterine quiescence and for the retardation of labor.

Nitric Oxide Synthase Sensitivity to Calcium During Labor

Sensitivity of NOS activity to calcium in cytosolic and membrane bound fractions during pregnancy was compared to that observed during labor. The method was according to Example 4.

Full thickness sections of rat uterus from 3 preterm gravid rats and 3 rats undergoing labor were stained by NADPH-diaphorase to localize NOS.

The activity of the NOS was determined by measuring the conversion of $^3$H-arginine to $^3$H-citrulline using crude cytosolic and particulate sub-fractions prepared from uteri removed from pregnant and laboring rats.

The production of $^3$H-citrulline was shown to be dependent on NADPH (data seen in FIG. 6), and was shown to be linear with time and protein concentration. Basal NOS activity (1 mM EGTA, no added calcium) was present in both, the soluble and the particulate cellular subfractions.

Histochemically, in the preterm gravid rat uterus sections, NOS was found to be localized within the myometrial neuronal varicosities, in the fine nerves surrounding blood vessels, in the vascular endothelium and in the entire decidua. The laboring rat uterus sections showed only minimal NOS staining in the decidual remnant and in the neural plexi within the myometrium.

NOS activity and its dependency or calcium and calmodulin was different in the cytosolic and membrane fractions as well as in the pregnant and laboring uterine samples with difference in scale reaching ratio about 1:3 for cytosolic v. membrane fraction. Results are shown in FIGS. 7A and 7B.

Figure 7A:
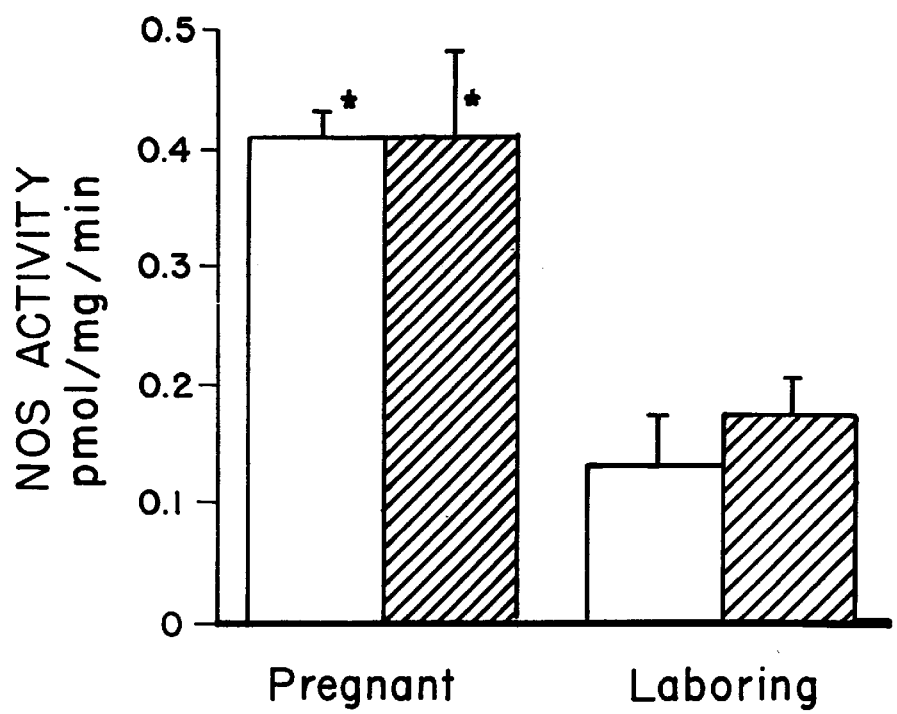
FIG. 7 depicts NOS activity found in cytosol in pregnant or laboring rat uterus (FIG. 7A), and in membrane bound NOS in pregnant and laboring rat uterus (FIG. 7B).

FIG. 7A illustrates NOS activity (in pmol/mg/min) found in the cytosol. NOS activity (N=5) in the cytosolic subfraction was measured independently of calcium and calmodulin (−CaCM in white). Activity decreased significantly (p<0.05) from pregnancy to labor. NOS activity measured in the presence of 3 mM calcium and 50U calmodulin (+CaCM in gray) represents additional activity that is dependent on the presence of calcium. The decrease from pregnancy to labor in this group was also significant where p<0.05.

In both these groups of uterine NOS activity found in cytosol, the activity of NOS found in laboring uterus was significantly, about 63%, lower than in the pregnant uterus.

Figure 7B:
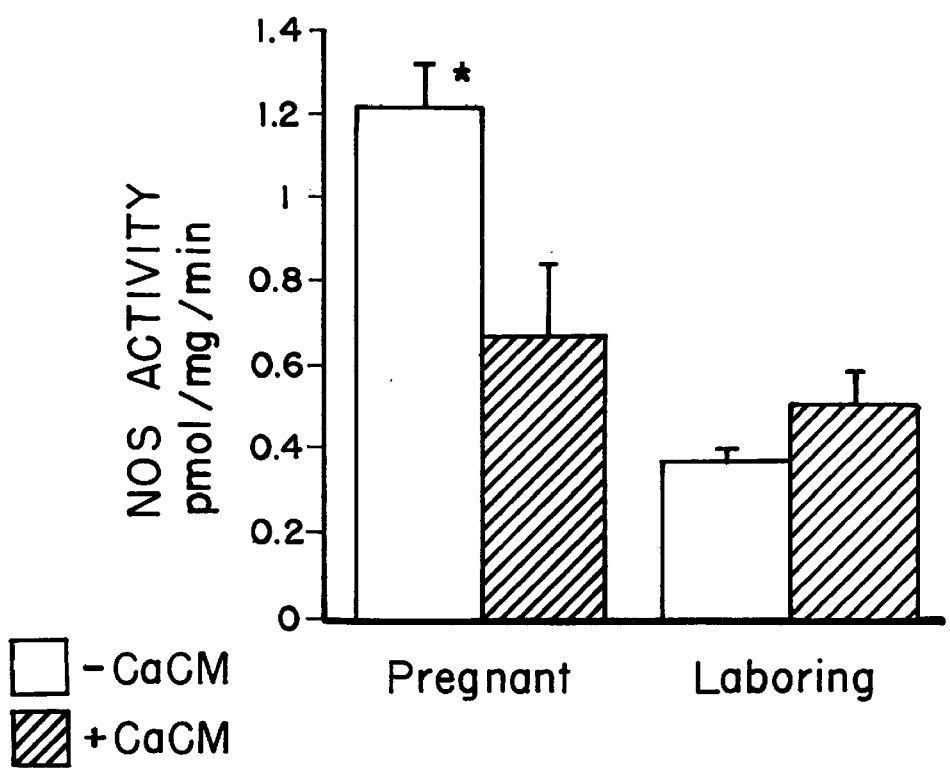

FIG. 7B illustrates NOS activity found to be membrane bound. NOS activity (N=5) in the particulate subfraction was measured in the absence (−CaCM) and presence (+CaCM) of 3 mM calcium and 50U calmodulin. The decrease in NOS activity in the −CaCM group was significant (p<0.05), while NOS activity that was dependent upon the presence of calcium and calmodulin (+CaCM) did not change significantly from pregnant to laboring tissue. The greatest portion of the total enzyme activity was measured in the membrane bound subfraction. The total calcium insensitive NOS activity in pregnant uterus was around 1.2 pmoles/mg/min., while the total calcium sensitive activity was around 0.7 pmoles/mg/min. As seen in Table 2 in laboring uterus, the activity of calcium insensitive NOS decreased by about 68% while the activity of calcium sensitive NOS decreased only about 25%.

The addition of calcium and calmodulin increased NOS activity. Two different enzymes, a calcium-sensitive and a calcium-insensitive form of the NOS were present in both uterine subfractions although the calcium dependent activity in the soluble fraction was minimal. In uteri of laboring rats, the basal and the calcium-stimulated activities of both the NOS enzymes were significantly reduced. Despite the fact that the overall activity of NOS was reduced in laboring uteri, the higher activity of the calcium augmented versus the basal activity of NOS in laboring uteri indicated a differential reduction in the calcium-insensitive isoforms(s) of the NOS enzyme. The results obtained are shown in Table 2 below.

TABLE 2

Decrease in NOS Activity from Pregnancy to Labor

| location | calcium dependence | % decrease in activity |
| --- | --- | --- |
| cytosol | − | 68% * |
| cytosol | + | 59% * |
| membrane | − | 69% * |
| membrane | + | 25% |

* $p < 0.05$ by one way ANOVA.

The activity of both the calcium sensitive and insensitive forms of the NOS enzyme are present in the gravid rat uterus and these activities are reduced in laboring uteri. These changes in the activities of the NOS enzymes are consistent with a nitric oxide role in the maintenance of uterine quiescence during gestation.

The presence of NOS in the different uterine structures suggests the presence of multiple molecular forms of NOS in the uterus. NOS isoforms are biochemically defined by their molecular weight, location within the cytosolic or membrane bound compartments of the cell, sensitivity to stimulation by calcium and calmodulin, and constitutive versus inducible regulation of enzyme activity. The enzyme characterization data suggests there may be as many as four NOS isoforms from pregnancy to parturition which may facilitate labor. Inhibition of NOS activity by the arginine analogs, L-NMA and L-NA, and aminoguanidine, and by omission of NADPH cofactor as seen in FIG. 6, confirms that the measured activity is NOS. The NOS activities that underwent the greatest decline between the quiescent and laboring state of pregnancy were the calcium-independent activities present in the cytosol and membrane particulate subfractions. The calcium dependent and calcium independent NOS have distinct genes each of which is able to be regulated. The major difference is their ability to increase NOS expression activity by increase in calcium ion for eNOS and bNOS concentrations in brain and endothelial forms. Increased expression of iNOS is not stimulated by calcium ions.

In Vitro SNAP Inhibition of Contractions in Pregnant Rat Uterine Muscle Tissue

To determine the effect of nitric oxide donors on contractions of pregnant rat uterus, the effect of the nitric oxide donor SNAP on the occurrence of spontaneous contractions was tested using isolated pregnant rat uterine muscle strips suspended in tissue baths containing an oxygenated Krebs solution.

Uterine muscle strips from virgin and 18–19 day pregnant Fischer rats were isolated and mounted in jacketed tissue baths and connected to isometric force transducers. The changes in tension versus time were displayed on a computer-generated polygraph. The muscle strips were maintained in standard oxygenated Krebs solution at 37° C. The mechanical responses to L-arginine, D-arginine, nitric oxide donors nitroglycerin, sodium nitroprusside, diethylamino nitric oxide (DEA NO), and spermine and nitric oxide synthase inhibitors N-nitro-L-arginine (L-NA), and N-nitro-L-arginine methyl ester (L-NAME) were measured after spontaneous or agonist-induced contractions. Dose response curves were created and analyzed.

Nitric oxide released by nitric oxide donors causes relaxation of uterine smooth muscle when provided exogenously. Nitroglycerin relaxes the uterine strips in a dose dependent manner. Diethylamino nitric oxide, which liberates nitric oxide, spontaneously and significantly relaxes uterine tissue. In the virgin (n=2) and gravid rats (n=4) uterine contractility was not significantly affected by inhibition of nitric oxide synthase with L-NA or L-NAME. Both L- and D-arginine added to the tissue bath caused a significant decrease in spontaneous and oxytocin-induced uterine contraction that lasted approximately 5 minutes. These results suggest that endogenous uterine nitric oxide exists and that D-arginine may be converted to L-arginine.

Within the uterine wall, the NOS is expressed in a form which is active in the production of NO. NO, whether endogenous or exogenous, is an inhibitor of uterine contractions, and its production within the uterus serves a physiologic role to prevent contractions so that gestation may be maintained long enough to allow fetal development. The loss of such a physiologic inhibitor of contractions would be predicted to be the cause of pre-term labor.

It has been now discovered that the amount of NOS expressed by the uterus is determined by the pattern of hormones produced by the mother in the uterus and elsewhere in her body. In pregnancy, the production of numerous hormones is increased and the expression of the NOS gene in uterine cells is also increased. Based on studies conducted in rodents, certain hormones made by the pregnant uterus, such as CSF and TGF-β are capable of increasing the expression of the gene for one form of NOS in the uterus. The form of NOS which is produced in greater amounts is active at any level of intracellular calcium, that is it is calcium-independent, and is homologous or similar to the iNOS.

Figure 8A:
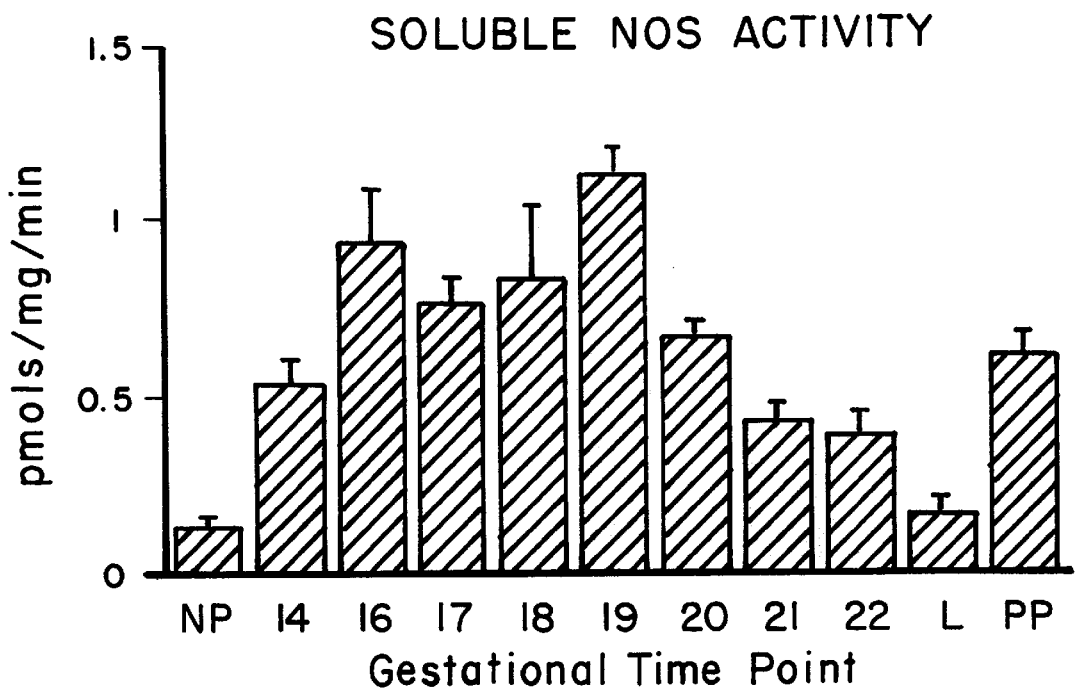
FIG. 8 is a graph depicting calcium independent NOS activity (FIG. 8A) in the soluble subfraction of the cell and (FIG. 8B) in the particulate subfraction of the cells, at varying time points before, during and after pregnancy.
Figure 8B:
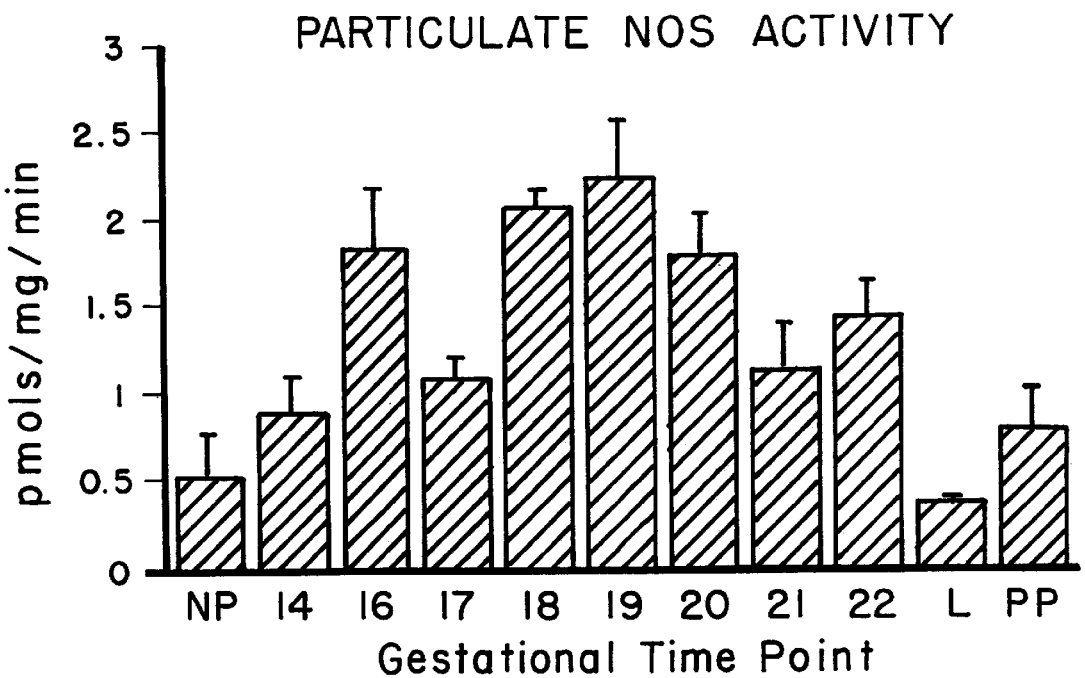

The uterus of the pregnant rat contains nitric oxide synthase (NOS) activity and this activity increases during gestation. Quantitation of calcium-independent inducible form of NOS activity in subcellular fractions of uteri from rats which were either nonpregnant, pregnant at days 14–22, or laboring, is seen in FIGS. 8A and B. NOS enzyme activity was present in crude soluble and particulate subfractions of uterine homogenates at each time point examined. Both soluble (FIG. 8A) and particulate (FIG. 8B) calcium-independent NOS activity were present. The particulate calcium independent NOS activity seen in FIG. 8B was consistently higher than the soluble calcium independent NOS activity seen in FIG. 8A. Calcium-independent NOS activity in both fractions was lowest in the nonpregnant state, and increased gradually from day 14 to a peak in activity at day 19 ($p<0.05$ by one way ANOVA). Enzyme activity decreased gradually from day 20 until the onset of labor, at which time NOS activity was comparable to that measured in non-pregnant uterine samples ($p<0.05$ by one way ANOVA). This study revealed a gradual increase in iNOS activity throughout pregnancy followed by a decrease in iNOS activity at term in both soluble and particulate NOS activity.

The inducible isoform of NOS is expressed in the uterus in a pregnancy-dependent manner. Localization of iNOS mRNA reveals expression in both the decidua and myometrium. Primary uterine myocytes express NOS enzyme activity and iNOS mRNA. Increased expression of NOS in the pregnant uterus have been found to be induced in the uterus by the condition of pregnancy.

In order to determine how the signalling system for NO production is regulated, the molecular isoforms of NOS present in the uterus and the cellular sites of NOS expressions were investigated during gestation. The cDNA for NOS isolated from brain (bNOS) from endothelial cells (eNOS) and from macrophage (iNOS) was previously described. Putative iNOS cDNAs were isolated as a part of the invention from a pregnant mouse uterine library and are being sequenced.

Since enhanced NOS activity in the pregnant uterus was found, a cDNA expression library in the lambda gt11 vector was constructed. Polyadenylated mRNA from the uterus of a pregnant mouse at day 16 of gestation was used as the source. The procedure was done using the basic protocol supplied with the Stratagene Zap cDNA protocol, Stratagene La Jolla, Calif., and lambda gt11 vector. The resulting library originally contained greater than 80% white plaques with an average insert size range 0.5 to approximately 3.5 kb and has a titer of $1 \times 10^{10}$ pfu/ml after plate amplification.

Screening with the 600 bp putative brain/endothelial RT-PCR clone failed to detect positive signals. The cDNA for mouse iNOS was used next to screen this library, and resulted in the isolation of seven clones which were positive when screened with the same probe in a southern analysis of the EcoR1 digests of the lambda DNA. Sequencing results revealed four potential iNOS sequences with probable homology to NOS. The largest clone is approximately 2100 bp in length, and thus is a likely a partial sequence or codes for a smaller enzyme. On the basis of available information, it is likely the uterus expresses an iNOS-like enzyme essentially identical to the original macrophage enzyme as macrophage-related cells are present in the pregnant uterus from which the cDNA library was constructed and iNOS-like sequences isolated from at least three other tissues including vascular smooth muscle are essentially identical to the macrophage enzyme.

Mouse uterine NOS activity expression appeared to be maximal at days 15–16, that is at a point of approximately 80% gestation. NOS enzyme activity in the mouse uterus was investigated in terms of conversion of arginine to citrulline (Example 4), sensitivity to cofactors NADPH (Example 4), calcium/calmodulin and NOS subcellular localization. Relative molecular size and similarity of NOS isoforms was examined by Western blotting.

Western analysis was performed on tissue extracts as well as on membranous subfractions using antisera reactive with eNOS, bNOS, and iNOS. Isoform-specific cDNA templates were prepared for characterization of NOS isoform-specific probes. These templates were cloned from mouse RNA by RT-PCR using primers directed to regions of divergence among the three NOS forms (putative heme binding domains) and their specificity was determined by Southern analysis.

Figure 9:
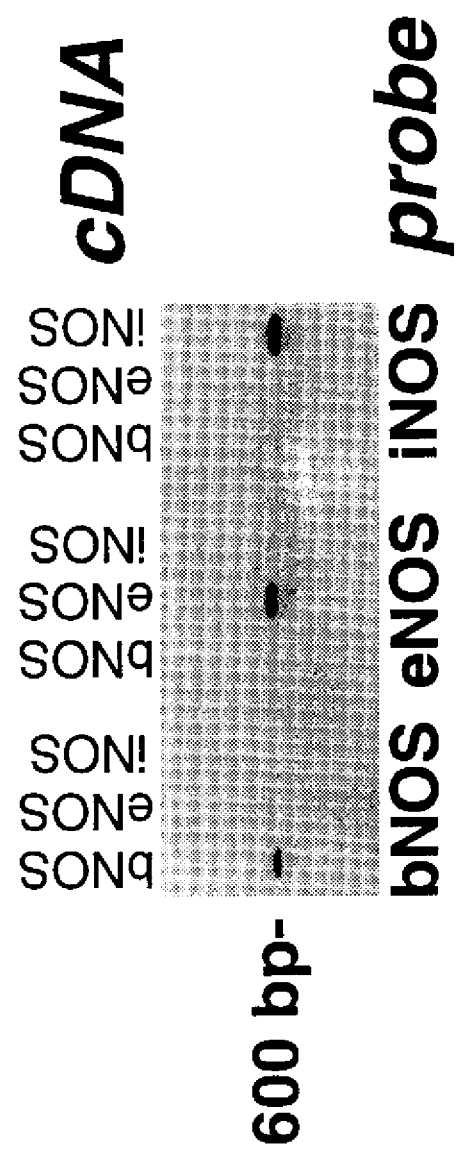
FIG. 9 is the Southern analysis of cDNA probes specific for each of the three known isoforms of NOS.

FIG. 9 is the Southern analysis of cDNA probe specific for each of the three known isoforms of NOS. The RT-PCR cloned cDNAs specific for each isoform were restriction-digested to release the ca 600 bp inserts, resolved from vector DNA by gel electrophoresis, transferred to nitrocellulose paper and probed with the indicated $^{32}$P-labeled probe. The autoradiogram from this analysis is shown.

FIG. 9 shows that the probes recognize only one NOS isoform. Although isolated from the mouse, cRNA probes were found to perform equally well in protection analyses of either mouse or rat mRNAs, reflecting the minimal sequence divergence between these species in the region used for the probes.

Figure 10:
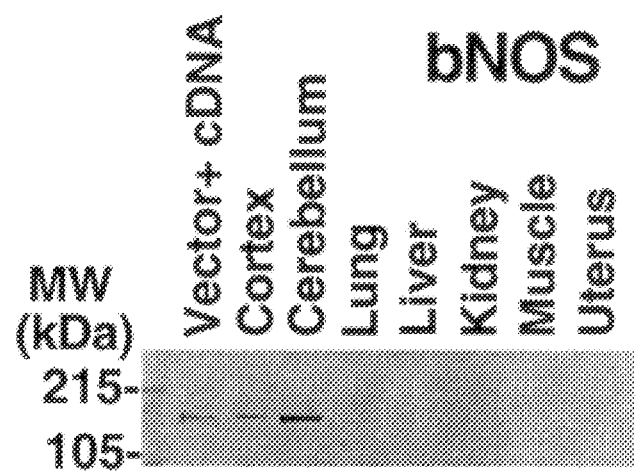
FIG. 10 is a Western analysis of protein samples probed with rabbit polyclonal antiserum to determine specificity of bNOS antiserum.

Tissue specificity with regard to various NOS isoforms was studied using Western analysis and is illustrated in FIG. 10.

Isoform-specific polyclonal antisera were developed by expression of full-length cDNAs for each isoform in a generally used fibroblastic kidney cell line immortalized by $SV_{40}$ transformation (COS-1) cells and immunization with SDS-PAGE purified proteins. Western blot studies were performed to characterize the specificity of polyclonal antisera to the eNOS and bNOS enzyme proteins. In addition, a commercially produced monoclonal antisera against iNOS (Transduction Laboratories, Lexington, Ky.) were evaluated. The specificity of the bNOS antisera is shown in FIG. 10, which demonstrates that the uterus and other non-neuronal tissue expresses very little bNOS.

FIG. 10 is Western analysis for determination of specificity of bNOS antiserum. Shown is a western blot of protein samples probed with rabbit polyclonal antiserum raised to the COS cell expressed protein from the full-length cDNA for bNOS. Lane 1 shows the signal from the expressed protein, demonstrating that the antisera recognizes the immunogen. The only tissue where the bNOS was detected were brain cortex and cerebellum.

Figure 11:
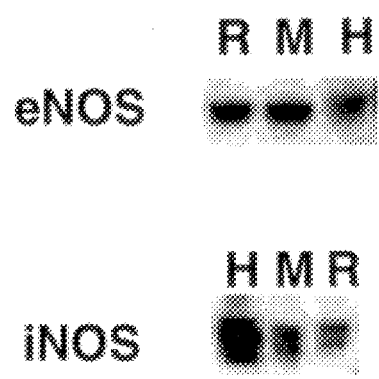
FIG. 11 shows reactivity of NOS expressed in the uteri of different species.

The ability of antisera for eNOS and iNOS to detect these proteins in mouse (M), rat (R), human (H) uteri is shown in FIG. 11. Since the human sample consisted of myometrium only, this result demonstrates the expression of iNOS in the muscle layer of the human uterus.

FIG. 11 is the Western analysis used for determination of reactivity of NOS expressed in the uteri of different species. Shown are the signals from 100 $\mu$g of protein extracts from pregnant day 17 rat (R), day 15 mouse (M) and 26 wk human (H) uteri probed with the indicated rabbit polyclonal antisera. As seen in FIG. 11, all three species expressed eNOS and iNOS in pregnant uteri.

Figure 12:
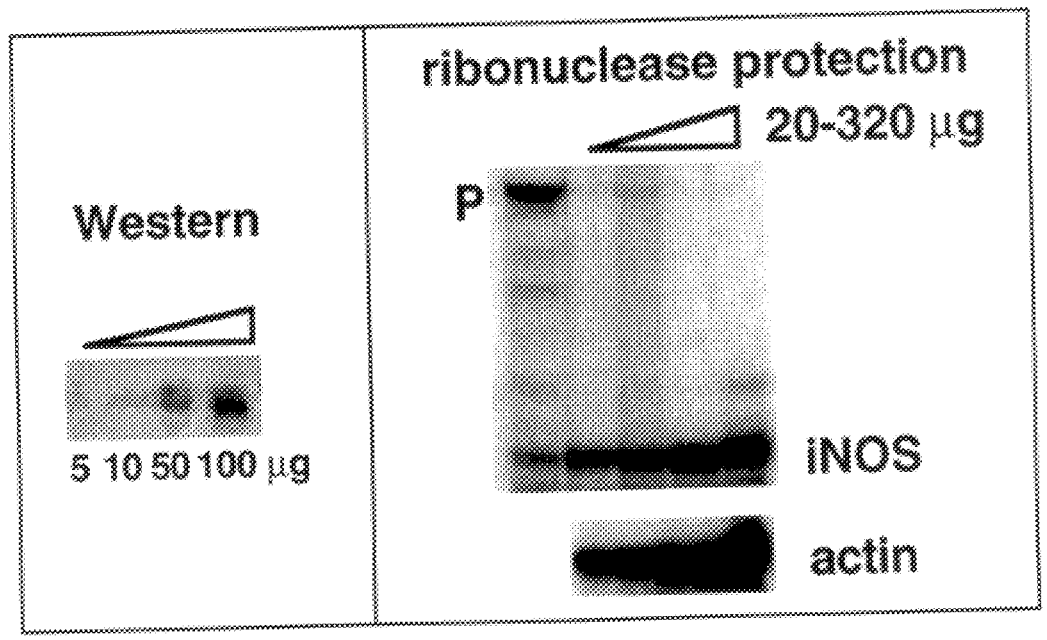
FIG. 12 is an autoradiogram of the signal obtained from the uterine protein extract probed with an anti-iNOS antiserum showing dependence of signal on the concentration of protein, or on RNA concentration in a ribonuclease protection assay for iNOS mRNA.

The concentration dependency of the signals in the Western and ribonuclease protection analyses is shown in FIG. 12 and is indicative of a specific signal.

FIG. 12 illustrates dependence of signal on the concentration of protein or RNA for iNOS assay. Shown is (left) autoradiogram of the signal obtained from 5 to 10 $\mu$g of uterine protein extract rat, at day 17 of pregnancy probed with a commercial anti-iNOS primary antiserum, peroxidase-conjugated goat anti-mouse IgG secondary antisera, and detected by enhanced chemiluminescence (Renaissance, New England, Nuclear-Dupont). A similar dependency is shown (right above) for iNOS mRNA detection by ribonuclease protection assay. Samples containing the indicated 20–320 $\mu$g amount of rat uterine total RNA at day 18 of pregnancy, were hybridized to the $^{32}$P-labeled rat iNOS cRNA probe, digested with ribonuclease, and resolved on a 5% polyacrylamide/8M urea gel. The position of the undigested 390 bp probe control (P) is shown along with 270 bp protected fragment (iNOS). Also shown (right below) is the corresponding positive control for RNA loading which was included with iNOS probe, and consists of a 105 bp protected fragment corresponding to beta-actin. The undigested actin probe was 170 bp in length. Some compression of the lanes is evident in the lower portion of the gel.

Figure 13A:
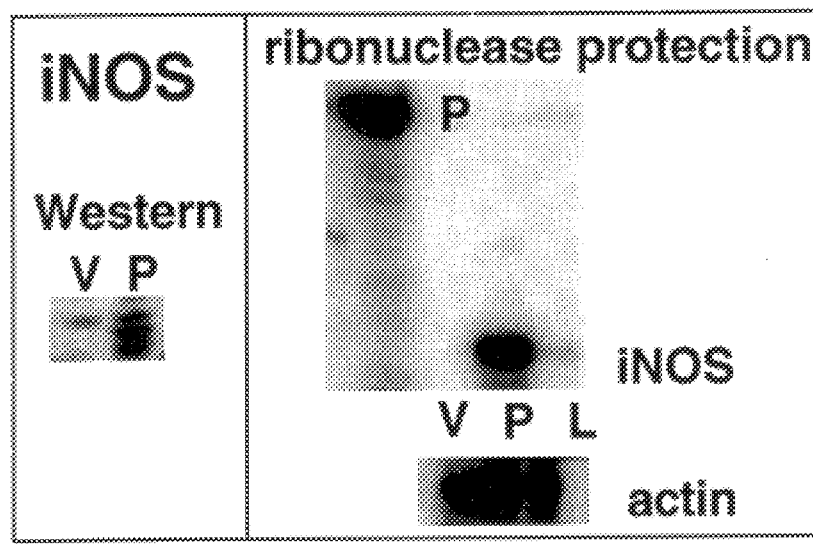
FIG. 13 illustrates the effect of pregnancy on the uterine expression of iNOS (FIG. 13A), eNOS and bNOS (FIG. 13B).

The presence of increased levels of NO and increased activity of NOS was described above and is shown in FIGS. 5–8. Now it has been found that pregnancy increases the uterine expression of iNOS protein and mRNA. Analysis of uterine iNOS expression reveals a pregnancy-dependent increase in both mRNA and enzyme protein (FIG. 13A). In contrast, uterine eNOS expression does not appear to be modified by pregnancy, and bNOS mRNA is not detectable in the uterus (FIG. 13B).

FIG. 13A illustrates how pregnancy affects the uterine expression of iNOS. A Western blot analysis, shown on the left, of iNOS protein extracts (100 μg) from virgin (V) and day 16 pregnant (P) mouse uterus. Shown on the right is a protection analysis of total RNA (40 μg/sample) prepared from virgin (V), pregnant at day 19 (P) and laboring (>1 pup delivered, L) rat uteri, and the corresponding actin controls. Upper P indicates undigested iNOS probe control. Assay conditions are as described in FIG. 12.

Figure 13B:
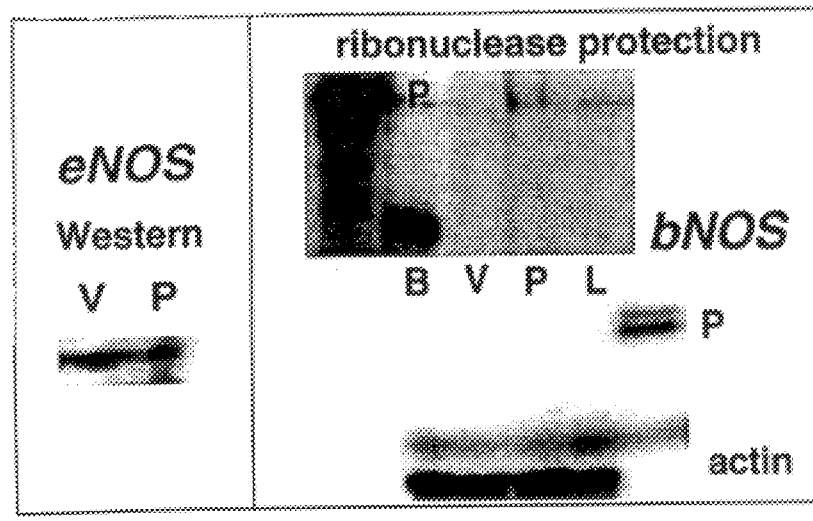

FIG. 13B illustrates expression of eNOS and bNOS in the uterus. FIG. 13B, left panel is a Western analysis of protein extracts prepared from virgin (V) and day 16 pregnant (P) mouse uterus probed with a rabbit polyclonal antiserum raised against COS cell expressed heme binding domain of eNOS protein and a peroxidase-coupled donkey anti-rabbit secondary antiserum (Amersham), and then visualized by enhanced chemiluminescence. The 130 kDa band corresponding to eNOS is shown. In the panel on the right, the results protection analysis of uterine RNA with the bNOS probe (P) is shown. The signal from 40 μg of uterine RNA from virgin, pregnant and laboring rats is shown along with the same amount of rat brain RNA run as a positive control. The corresponding actin loading controls and probe (P) ar shown below the bNOS bands. Assay conditions are as in FIG. 12.

Inducible NOS, (iNOS) seems to be the NOS isoform most relevant to pregnancy and to gestational quiescence. The failure to detect bNOS and mRNA even in the virgin uterus suggests that the neuronal cell bodies are located outside the uterus.

Additionally to the Western blot analysis, in situ hybridization for localization of iNOS expression in the pregnant uterus was performed. Results are illustrated in FIG. 14.

Figures 14A, 14B, 14C, 14D:
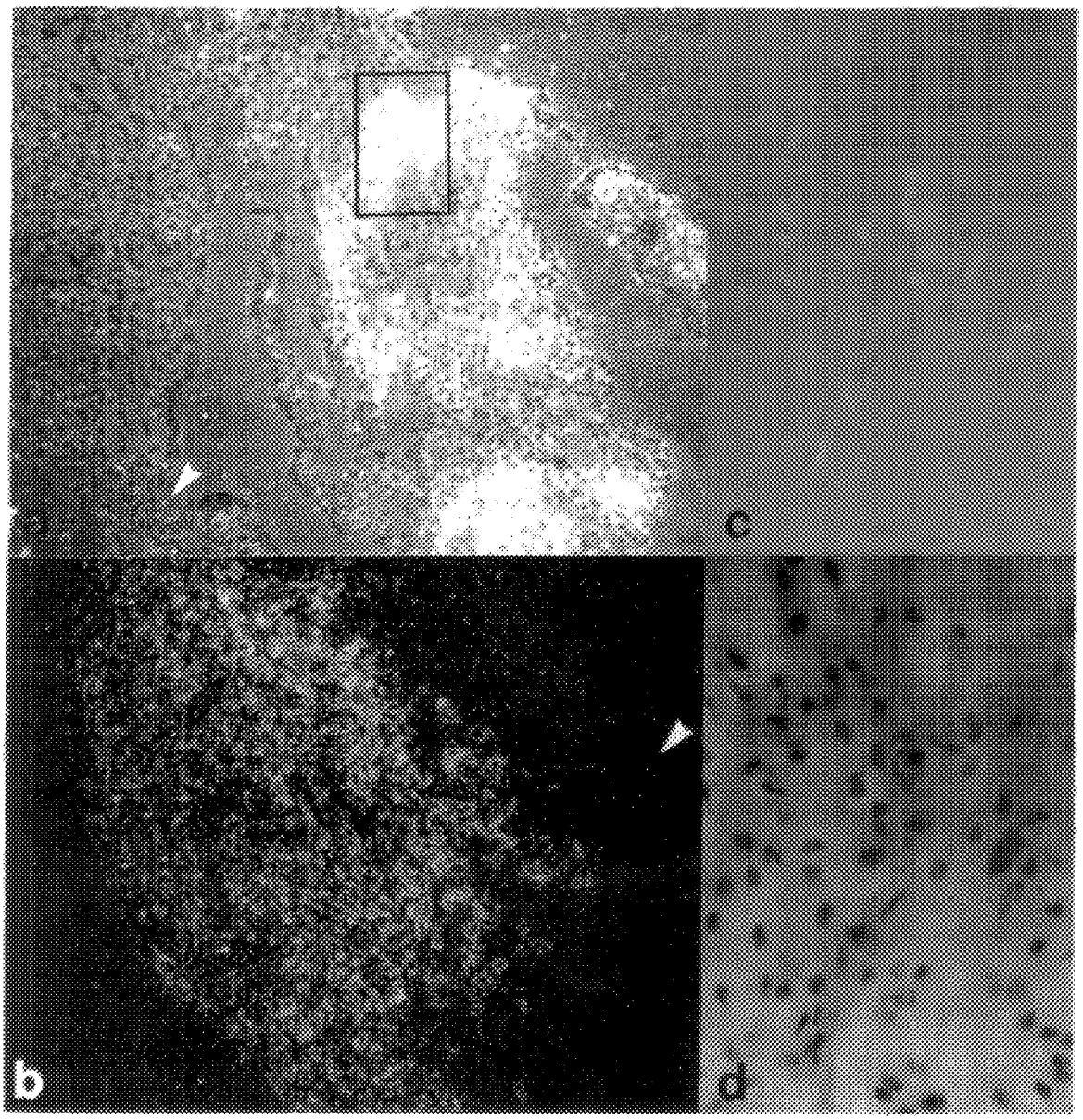
FIG. 14 is a photograph of in situ hybridization with a rat iNOS cDNA antisense probe for localization of iNOS expression in the pregnant rat uterus at day 16 (FIG. 14A); in the decidua basalis (FIG. 14B), in myocytes (FIGS. 14C and 14D).

FIG. 14 illustrates localization of iNOS expression in the pregnant rat uterus at day 16 of gestation. In-situ hybridization was performed using a rat macrophage cRNA antisense probe. Panel (a), darkfield image of the uterus showing the area detailed (box) in panels (c) and (d). The area of intense signal is longitudinal myometrium which separated from the circular myometrium during sample preparation (×100). Arrowhead indicates the same area on panel (b), which is a continuation of the same section shown in (a), and is also a darkfield image. Panel (b) shows iNOS expression in the decidua basalis but not in the stroma (×200) Panel (c) is epiluminescent imaging of the silver grains above the myocytes (×400). Panel (d) is bright field image of the same are shown in (c), showing the silver grains as brown deposits over the muscle cells (×400).

FIG. 14 demonstrates specific staining of cells, in both the decidual and myometrial layers of a rat uterus at day 16 of gestation. Within the muscle layers, iNOS was expressed in myocytes, panels (c) and (d), but expression was not as uniform as in the decidua.

Staining was also apparent in the decidua basalis, where the signal was more intense and more uniform than in the muscle layer. NO signal was detected in the remaining portion of the decidualized endometrium. The endometrial stroma of the mouse contains cells of hemopoietic origin which differentiate in pregnancy to decidual, macrophage and granulated material gland cells.

NO has been found to suppress contractility of pregnant uterus and therefore, the smooth muscle cells would be the ultimate target of NO in suppression of contractile activity during gestation. To determine whether there is increased NO and/or NOS activity, primary myocytes from the pregnant mouse uterus were investigated for expression of NOS activity and iNOS mRNA. Results are illustrated in FIG. 15.

Figure 15:
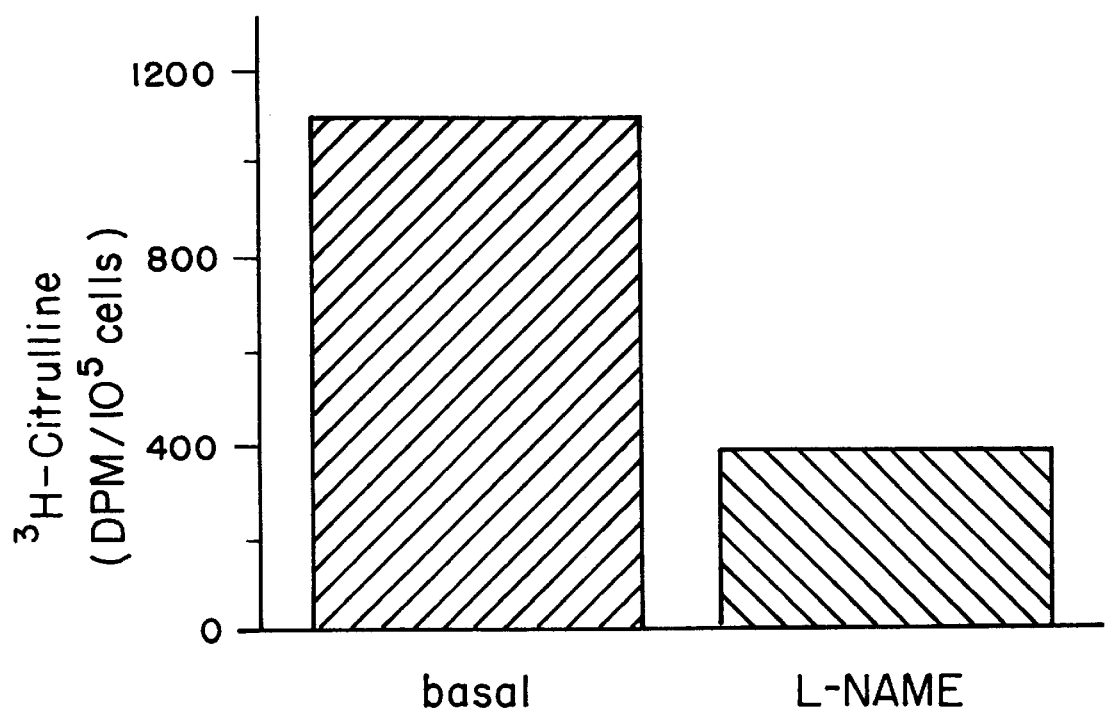
FIG. 15 is a graph showing NOS activity in primary mouse uterine myocytes in the presence or absence of NOS inhibitor L-NAME.

FIG. 15 shows the presence of NOS activity in primary myocytes. Shown are the results of the assay of intact primary myocytes prepared from a mouse uterus at day 15 of gestation and plated for 48 hours. The cells were pulse labeled with $^3$H arginine (S.A. 69 Ci/mmol) for 30 minutes in the presence or absence of the NOS inhibitor L-NAME (1 mM) and processed for determination of $^3$H citrulline production as described in Example 4. The results (mean SE) of a representative experiment performed in triplicate wells are shown. Because the amount of endogenous arginine is not known under the active metabolic conditions present in intact cells, the data are expressed as DPM rather than molar amount of citrulline. NOS activity is defined as the difference in DPM in the presence and absence of L-NAME, nitro arginine methyl ester, a competitive inhibitor of NOS, and was approximately 700 DPM in this experiment.

FIG. 15 shows that myocytes exhibit NOS activity and that such activity is inhibited by known NOS inhibitor L-NAME.

To investigate whether these same cells express iNOS mRNA, ribonuclease protection assay was used on primary uterine myocytes and the effect of pregnancy-related cytokines on iNOS induction in uterine smooth muscle cells isolated from gravid mice was examined. Results are shown in FIG. 16.

Figure 16:
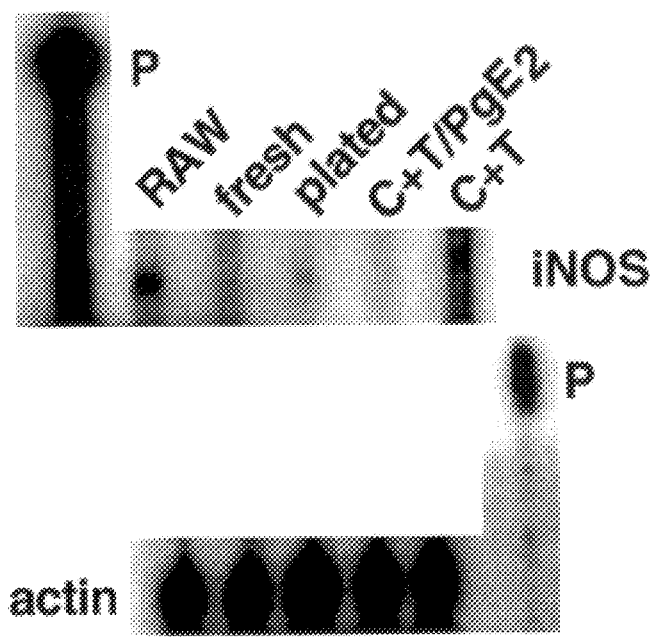
FIG. 16 is a graph illustrating cytokine regulation of NOS activity in primary uterine myocytes.

FIG. 16 shows results of an effect of cytokines on primary uterine myocytes iNOS MRNA expression and assay of iNOS mRNA by ribonuclease protection is described in Example 9. Myocytes were prepared from the uteri of pregnant mice at day 15 of gestation by enzymatic dispersion. Forty μg of total RNA from either myocytes or the murine macrophage line RAW 264.7 (positive control) was then assayed by ribonuclease protection assay.

Shown in FIG. 16 is the 270 bp protected fragment corresponding to iNOS in samples from (left to right), Inf-γ+LPS-induced mouse macrophage line RAW, day 15 pregnant mouse uterine primary myocytes prior to culture (fresh), after 24 hour in culture without cytokines (plated), plated in the presence of CSF (100 ng/ml) plus TGF-β (20 ng/ml) plus PgE$_2$ (10 μM), (C+T/PgE$_2$) and in the presence of CSF and TGF-β alone (C+T). All samples contained 40 μg total RNA. Lane 1 contained the undigested iNOS probe (P) control at 1:1000 dilution. The lower panel shows the corresponding β-actin control signal (actin) and undigested probe control (P).

The level of iNOS expression by the uterine myocytes is significantly less than that of the cytokine-activated murine macrophage cell line RAW. However, given the shorter diffusion path in an autocrine/intracrine signalling mechanism of myocyte-derived NO acting upon itself, the level of NOS expression required for physiologic effect may be expected to be much lower. Therefore, the observed level of iNOS expression in the uterine myocytes may be considered of potential physiologic relevance.

Treatment with CSF-1 plus TGF-β1 resulted in an approximately three-fold increase in iNOS activity and an increase in iNOS mRNA. Pretreatment with dexamethasone prevented the increase in NOS activity. These results demonstrate and confirm that mouse uterine smooth muscle cells have the capacity to express iNOS, and that this expression can be augmented by treatment with a novel combination of extracellular signalling molecules which are normally present in the uterus during pregnancy.

A potent uterine relaxant is made in greater amounts at a time when the uterus undergoes a state of profound refractoriness to stimulation. The increased levels of iNOS are found within the pregnant rat uterus where it is expressed in both the decidual and myometrial layers. These findings strongly support the view that NO participates in the quiescing mechanism.

The expression of iNOS in a large number of tissues including smooth muscle cells is known to be positively and negatively regulated by a variety of growth factors and certain cytokines which are participate in the inflammatory response to immune cell activation. For example, iNOS expression can be induced by IL-1β, TNFα, or INFγ+ endotoxin. Transforming growth factor beta, in contrast, has been demonstrated to destabilize iNOS mRNA, and thereby oppose the inductive process.

Cytokines (as defined) are hormones present in the pregnant uterus. Cytokine IL-1β is present in decidua and placenta; IL-6 is present in trophoblast, chorion decidecum, IL-8 is present in chorion; TNFα is present in decidua, placenta, amniotic fluid and is increased by estrogen (E)b and progesterone (P); CSF-1 is present in decidua and placenta and increased by E and P; TGFβ is present in decidua, placenta and chorion; INFγ is present in placenta, and $PgE_2$, is present in decidua and amnion.

To determine whether the myometrium was a site of nitric oxide synthesis, nitric oxide synthase activity induction was studied in primary mouse uterine myocytes.

Cytokine regulation of NOS activity in primary uterine myocytes is illustrated in FIG. 17. Myocytes were isolated from the scraped uteri of pregnant mice at day 15 of gestation by enzymatic dispersion. The cells were plated overnight, then treated 16 to 18 hours with the cytokines or vehicle (basal), and pulse-labeled for 1 hour with $^3$H L-arginine (20 µCi/ml, specific activity 69 Ci/mmol). The data are expressed as fold of basal activity and represent the $^3$H citrulline production which can be inhibited by the addition of the NOS inhibit L-NAME (1 mM). FIG. 17A (top), treatment with endotoxin (LPS, 10 µg/ml) plus interferon (γ-IF (100 u/ML); interleukin-1 β (IL-1, 20 ng/ml) plus tumor necrosis factor alpha (TNF-alpha, 100 ng/ml); macrophage colony stimulating factor (mCSF, 100 ng/ml); transforming growth factor beta (TGF-beta-1, 20 ng/ml); and CSF plus TGF together.*, p<0.05. FIG. 17B (bottom), prevention of CSF+TGF-stimulated NOS induction by co-incubation (C/T) with either dexamethasone (DEX, 10 µM) or prostaglandin $E_2$ ($PGE_2$, 100 µM) in the presence of meclofenamate (20 µM). The data are expressed as means ±SEM for n=5–6. * means significant difference from control (basal or CSF/TGF, respectively) by one-way ANOVA p<0.05.

At this point in gestation, about 70% NOS activity was present in the myocytes. NOS inhibitor L-NAME inhibited NOS activity of control myocytes. The $Ca^{2+}$ ionophore A23187 (1 µM, 10 min.) failed to further stimulate myocyte NOS activity. These results indicate that NOS present in myocytes is different from calcium dependent constitutive neuronal and endothelial NOS isoforms, and resembles inducible forms of NOS.

The cytokines TGF-β1 and CSF-1 were chosen for this study because concentration of both have been shown to increase within the uterus throughout pregnancy. LPS and γ-IF, IL-1 and TNF-α were also tested to compare uterine myocyte NOS response to known inducers of macrophage and vascular smooth muscle NOS.

Incubation of the cell cultures for 24 hours with LPS γ-IF, IL-1β/TNF-α, CSF, or TGF-β1 caused no significant change in NOS activity. However, treatment with CSF-1 in the presence of TGF-β1 caused a significant increase in NOS activity (5.1±1.1 fold of basal, p<0.01 by one-way ANOVA, Scheffe post hoc test, n=6). TGF-β1 dose responses were linear in the range of 0.2–20 ng/ml. Inhibition of eicosanoid synthesis by the addition of $10^{-5}$ meclofenamate to culture media shifted the dose response curve for TGF-β1 to the left. CSF/TGF induction was inhibited by L-NAME, dexamethasone and $PGE_2$.

These in vitro experiments show that smooth muscle cells isolated from the gravid mouse uterus express a form of NOS activity which is responsive to and induced by cytokines, and is inhibited by the presence of prostaglandins, particularly by $PGE_2$. The suppressive effect of prostaglandins on iNOS expression and activity suggests that such suppression may be a cause of labor in that prostaglandins are used to induce labor and abortion. The cytokine response differs from the classic induction response seen in macrophage or vascular smooth muscle NOS, further confirming the presence of a unique form of NOS regulation in the uterus which would be a critical component of any uterine-specific mechanism for the autoregulation of myometrial contractility by nitric oxide.

Characterization of Nitric Oxide Role in Normal Pregnancy and Preterm Labor

Nitric oxide synthase is localized in myometrium, decidua, placenta, and uterine nerves. Changes in these areas in rat uterus were documented during pregnancy and delivery using histochemical staining as described above. NOS enzyme function was additionally assayed in non-gravid, gravid, and postpartum uterus.

Virgin, pregnant, and post-partum monkey uterus were used for nitric oxide synthase localization using diaphorase staining and arginine to citrulline enzyme assay as described in previously. In these samples, diaphorase staining was strikingly increased by pregnancy and NOS activity appeared to be concentrated in the branching neural network within the myometrium as well as in the decidua. Similarly to rat uterus, NOS activity changes were observed in monkey uterus in a progression from the non-pregnant to the pregnant and then the post-partum state. Uterine muscle strips consisting of full thickness (including decidua) or myometrium only were used to determine the layer of the uterus most responsible for nitric oxide mediated relaxation.

Studies of monkey uterus NOS activity and increase during pregnancy described above showed a strikingly higher diaphorase staining in gravid over non-gravid monkey uterus.

The all above discussed results of in vitro studies support the current invention and confirm results of in vivo studies which show that nitric oxide is directly involved in maintaining uterus relaxation during pregnancy. When the endogenous levels or availability of nitric oxide decrease, the uterus respond with increased contractility resulting in labor. When this occurs prior to normal term of pregnancy, such decreased level of nitric oxide results in preterm labor. By providing exogenous nitric oxide source or donor, the preterm contractions can be inhibited and the preterm labor stopped before resulting in preterm delivery. By providing agents hormones such as cytokines growth factors or sense or antisense oligonucleotides, the level of iNOS expression can be enhanced to prevent development or reverse onset of or stop premature labor.

VII. Clinical Studies

Treatment of preterm labor with known tocolytic agents, especially the virulent labor induced by hysterotomy for fetal surgery, has proven largely ineffective. Moreover, such treatment presents definite danger for both mother and the fetus because the somehow effective vasodilating concentrations of known tocolytics are too high and cause definite toxic reactions. After demonstrating in rhesus monkeys and in sheep that nitric oxide, a potent smooth muscle relaxant, ablated labor even after hysterotomy, nitroglycerin was tested during and after hysterotomy for fetal surgery in eight patients.

In an attempt to control strong hysterotomy induced contractions, it was surprisingly found that intraoperative uterine contractions responded to intravenous nitroglycerin given as a single injection or as a continuous infusion in three patients and nitroglycerin infusion was therefore used as the primary tocolytic in other patients undergoing hysterotomy and fetal thoracotomy. In contrast to all previous tocolytic regimens attempted in this setting, nitroglycerin infusion produced profound uterine relaxation and ablated postoperative preterm labor without apparent ill effect on mother or fetus.

Typically, uterine relaxation requires a depth of anesthesia which is known to produce myocardial depression in both mother and fetus. Regimen of postoperative tocolysis using magnesium sulfate and betamimetics as well as indocin proved inadequate because doses required to suppress uterine activity proved toxic for mother and dangerous for the fetus. Specifically, maternal volume restriction thought necessary to avoid pulmonary edema when using high-dose magnesium sulfate and terbutaline produces uteroplacental hypoperfusion, and indocin can produce right-heart failure manifested in patients by tricuspid regurgitation.

Based on experimental work in in vivo monkeys and sheep and in vitro rat uterus and on the initial clinical experience over the past decade, a regimen was developed in which a nitric oxide donor, such as nitroglycerin infusion was used as primary tocolytic agent during and after fetal surgery. The regimen is described in Example 6.

The effect of nitroglycerin on the preterm uterine contractions after uterine manipulation was originally studied in patients undergoing fetal surgery.

Following the hysterotomy, patients experienced several episodes of visible and palpable uterine contractions. In three patients, these contractions were treated with single intravenous doses of 50–100 $\mu$g nitroglycerin intravenously. Within 5–10 seconds the contracted uterus completely relaxed and the labor stopped. In the next two patients, the contractions were treated with an infusion of nitroglycerin. Response to demonstrated episodes of uterine contraction to nitroglycerin infusion resulted in ablation of contractions which persisted while the infusion continued.

The method of the current invention utilizes for the first time a nitric oxide donor drug for tocolytic management of preterm labor. Based on the hypothesis that nitric oxide was shown to be an important mediator of uterine smooth muscle relaxation, the ability of nitric oxide donor drugs to ablate preterm labor in the rhesus monkey and in laboring sheep, it has been now demonstrated that nitroglycerin ablates labor after hysterotomy in fetal surgery. The discovery that otherwise commonly used class of drugs has also a powerful tocolytic effect allows management of prevalent and devastating problem of spontaneous preterm labor. The potential for treating spontaneous or surgically induced preterm labor is particularly appealing because nitroglycerin and other nitric oxide donor drugs can be used effectively by a variety of routes including infusions, transcutaneous patches and sublingual depositories making chronic outpatient treatment relatively simple.

The discovery also eliminated original concerns about toxicity of nitroglycerin in pregnant women. In the studies supporting the invention, nitroglycerin infusion provided profound uterine relaxation during and after fetal surgery and appeared well tolerated by both mother and fetus. Use of nitroglycerin for tocolysis allowed reduced levels of inhalation anesthesia intraoperatively and modified the need for volume restriction and hemodynamically destabilising drugs postoperatively. Nitroglycerin infusion does, however, require continuous monitoring of mean arterial pressure and central venous pressure in an intensive care setting.

One major concern during development of this invention was that nitroglycerin infusion might have an ill-effect on the fetus. Although nitroglycerin and other nitric oxide donor drugs have been well-studied in the treatment of myocardial infarction, heart failure, and other clinical settings, they have not been extensively studied during pregnancy. While the effect on maternal hemodynamics is well-understood and predictable, possible hemodynamic adverse effects on uteroplacental perfusion and fetal hemodynamics were unknown. Exogenous nitric oxide was shown to increase uterine artery flow in monkey even though mean arterial pressure was decreased. But the major concern with nitroglycerin was that drug that crosses the placenta could dilate the normally constricted fetal vascular beds particularly the pulmonary vascular bed. Indeed, nitric oxide donor drugs given directly to the fetus do produce vasodilation and change blood flow distribution in fetal lambs. However, in acute studies in both sheep and monkeys these symptoms have thus far not been observed. No significant hemodynamic change or metabolic consequence for the fetus from infusion of high doses of nitroglycerin and other nitric oxide donor drugs was detected. Nitroglycerin was rapidly metabolized in the maternal circulation and its transplacental passage appeared to be poor, at least in the sheep, where it has been measured. Individual patient's case reports are described in Example 7.

It has now been shown that exogenous nitric oxide ablates preterm labor in monkeys and sheep and it was also demonstrated that nitroglycerin infusion produces profound uterine relaxation after hysterotomy for fetal surgery in humans. The effectiveness of exogenously administered nitric oxide sources in preterm labor confirms that endogenous nitric oxide production in the myometrium allows uterine relaxation to accommodate pregnancy and that withdrawal of nitric oxide-mediated uterine relaxation produces labor at parturition and that the pharmacologic manipulation of nitric oxide may provide the first effective treatment of preterm labor. Experimental work in rats, sheep and monkeys is consistent with these findings.

VIII. Pharmaceutical Compositions

One of the compositions of the invention finds an application in the retardation or inhibition of uterine contractions to prevent or retard labor, particularly preterm labor. Another composition of this invention finds an application in the induction or augmentation of uterine contractions to promote labor such as in the induction of parturition at maturity, and in the promotion of early termination of pregnancy.

a. Compositions for Control of Preterm Labor

This invention provides compositions suitable for control, inhibition and management of preterm labor.

The composition typically comprises a uterine relaxant selected from the group consisting of agents capable of potentiating the effect, or increasing the level, of nitric oxide in utero, such as nitric oxide donors, substrates, precursors and sources, and mixtures thereof.

Optionally, a second agent selected from the group consisting of other tocolytic agents, analgesics, vasopressors, and mixtures thereof are added to the nitric oxide source.

Nitric oxide source suitable for use in the composition of this invention that are capable of potentiating the effect, or increasing the level of nitric oxide in utero include S-nitroso-N-acetylpenicillamine (SNAP) and analogues thereof, nitric oxide nucleophiles or nitric oxide adducts such as diethylamino/nitric oxide, DETA/NO, spermine or other nucleophilic groups known in the art, nitroglycerin and analogues thereof such as isosorbide dinitrate, nitropaste, nitropatches, nitroprusside and analogues thereof, other nitrovasodilators such as hydroxylamine, sodium azide, 2-isosorbide mononitrate, PETN, and analogues thereof and endogenous precursors of nitric oxide such as L-arginine.

The nitric oxide source described above may be present in the composition in an amount of about 0.01 to 99 wt %, preferably in an amount of about 0.1 to 85 wt %, and still more preferably about 1 to 20 wt %. However, other amounts of the nitric oxide source are also suitable.

Specific agents may be present in the following amounts. SNAP and similarly acting compounds may be present in the composition in an amount of about 0.1 to 15 wt %, preferably about 0.5 to 10 wt %, and more preferably about 1 to 8 wt %. Nucleophile/nitric oxide adducts such as DEA/nitric oxide and similarly acting mixtures may be present in the composition in an amount of about 0.01 to 18 wt %, preferably about 0.1 to 15 wt %, and more preferably about 1 to 10 wt %. Nitroprusside and similarly acting agents may be present in the composition in an amount of about 0.01 to 10 wt %, preferably about 0.1 to 8 wt %, and more preferably about 1 to 5 wt %. Nitroglycerin and similar acting agents may be present in the composition in an amount of about 0.01 to 20 wt %, preferably about 0.5 to 10 wt %, and more preferably about 0.8 to 8 wt %. However, other amounts of these compounds are also suitable as long as they are not toxic to the mother or to the fetus.

Other tocolytic agents suitable for use in the labor retarding composition as the second agent include β-adrenergic agonists, oxytocin antagonists, prostaglandin synthesis inhibitors such as prostaglandin synthetase inhibitors, magnesium salts, calcium transport blockers, ethanol, phosphodiesterase inhibitors, and progestins, among others.

Typically, the other tocolytic agents may be present in the composition in an amount of about 0.01 to 90 wt %, and more preferably about 1 to 25 wt %. However, other amounts may also be utilized.

Among the tocolytic agents, preferred amounts for specific compounds are described below.

Within the context of this patent, a β-adrenergic agonist is defined as any compound or mixture of compounds capable of stimulating one or more types of β-adrenergic receptors. The β-adrenergic agonists may be present in the composition in an amount of about 0.01 to 10 wt %, and more preferably about 1 to 5 wt %, although other amounts are also suitable. β-adrenergic agonists suitable as tocolytic agents include epinephrin, isoproterenol isopropylnorepinephrine), p-hydroxyphenylisopropylarterenol), isoxsuprine, orciprenaline, (1-(3,5-dihydroxyphenyl)-2-isopropylaminoethanol sulfate, salbutamol, terbutaline, analogues thereof, and other agents known in the art A prostaglandin synthesis inhibitor is defined as a compound or mixture of compounds which inhibit any step or steps in the series of enzymatic reactions involved in the synthesis of prostaglandins. Prostaglandin synthesis inhibitors suitable for use as tocolytic agents include indomethacin (1-(p-chlorobenzoyl)-5-methoxy-2-methylindole-3-acetic acid), naproxen, aspirin, meclofenamic acid, phenylbutazone, analogues thereof, and other agents. The prostaglandin synthesis inhibitors may be present in the composition in an amount of about 0.01 to 90 wt %, and more preferably about 1 to 10 wt %. However, other amounts are also suitable.

Magnesium salts suitable as tocolytic agents include $MgSO_4$ and other inorganic and organic salts. The magnesium salts may be present in the composition in an amount of about 0.5 to 10 wt %, and more preferably about 5 to 20 wt %. However, other amounts are also suitable.

Within the context of this invention, a calcium transport blocker, a term herein used interchangeably with calcium channel-blocking agent, is defined as any compound or mixture of compounds capable of reducing importation of extracellular calcium. Calcium transport blockers suitable for use herein as tocolytic agents include nicardipine, nitrendipine, nifedipine, analogues thereof, and other agents known in the art. The calcium transport blockers may be present in the labor retarding composition in an amount of about 0.5 to 15 wt %, and more preferably about 1 to 20 wt %. Other amounts are, however, also suitable.

The progestins provided for use as tocolytic agents include progesterone, pregnanolone, pregnanedione, epipregnanolone, allopregnanolone, allopregnanedione, analogues thereof, and other agents known in the art. The progestins may be present in the composition in an amount of about 0.5 to 30 wt %, and more preferably 1 to 15 wt %. However, other amounts are suitable. The ethanol may be present in an amount of about 1 to 20 wt %, and more preferably about 5 to 15 wt %. However, other amounts are also suitable.

The phosphodiesterase inhibitors provided by the invention as suitable tocolytic agents include papaverine, aminophylline, cilostamide, valeramide, zaprinast, rolipram, amrinone, dipyridamole, theophylline, analogues thereof, and other agents known in the art. These inhibitors may be present in the composition in an amount of about 0.5 to 18 wt %, and more preferably about 1 to 10 wt %.

Other tocolytic agents, such as oxytocin antagonists, may be present in suitable amounts as known in the art, or in lower amounts taking into consideration the presence of the uterine relaxant agent in the composition.

The present composition may also include other agents typically used for administration to a preterm labor patient. Some of these agents such as, for instance, those intended for countering the side effects of the components of the composition, are listed below. However, other agents may also be incorporated in amounts that are known to the practitioner.

Analgesics for use in conjunction with the present nitric oxide source include acetaminophen, acetylsalicylic acid, morphine, fentanyl, or other similar acting agents known in the art, and mixtures thereof. The analgesics may be present in the composition of the invention in an amount of about 0.1 to 18 wt %, and more preferably about 5 to 20 wt %. However, other amounts are also suitable.

Vasopressors may be used in conjunction with the nitric oxide source to counter the vasodilating effect of the latter. Suitable vasopressors include α-adrenergic agonists such as ephedrine, norepinephrine, dopamine and epinephrine, analogues thereof, and other similar acting agents known in the art. The vasopressors may be present in the composition of the invention in an amount of about 0.01 to 10 wt %, and more preferably about 1 to 5 wt %. However, other amounts are also suitable as is known in the art.

The labor retarding composition may further comprise a pharmaceutically acceptable carrier. The pharmaceutically acceptable carrier may be polycarbophil, sucralfate, carboxymethylcellulose, β-cyclodextrin or other compounds known in the art. Other carriers known in the art that are pharmaceutically acceptable are also within the scope of this invention.

The following are preferred embodiments of the labor retarding composition.

In one preferred embodiment, the labor retarding composition comprises a uterine relaxant capable of potentiating the effect, or increasing the level, of nitric oxide in utero.

In another preferred embodiment of this invention, the labor retarding composition comprises a uterine relaxant selected from the group consisting of SNAP, nucleophile/nitric oxide adducts, nitroprusside, nitroglycerin, analogues thereof, and mixtures thereof.

In a more preferred embodiment, the composition comprises nitroglycerine, analogues thereof or mixtures thereof.

Further preferred is a labor retarding composition comprising SNAP, analogues thereof, or mixtures thereof.

Also preferred is a labor retarding composition comprising nucleophile/nitric oxide adducts such as DEA/nitric oxide, analogues thereof, or mixtures thereof.

Additionally preferred is a labor retarding composition comprising a uterine relaxant selected from the group consisting of nitroprusside, analogues thereof, and mixtures thereof.

In one particularly preferred embodiment of the invention, the labor retarding composition comprises a uterine relaxant selected from the group consisting of SNAP, DEA/nitric oxide, nitroprusside, nitroglycerin, analogues thereof, and mixtures thereof, and a phosphodiesterase inhibitor, and papaverine.

An additional preferred embodiment of the invention is a labor retarding composition comprising L-arginine, metabolic precursors thereof, analogues thereof, or mixtures thereof, along with a phosphodiesterase inhibitor such as papaverine or zaprinast.

For endogenous control of preterm labor through induction of increased production of NO by increased expression of iNOS, hormones, cytokines, growth factors, or sense or antisense oligonucleotides are administered in any suitable route described above.

b. Compositions used for Labor Induction

Also provided herein are labor promoting compositions to be used in a method for promoting uterine contractions that comprises administering to a pregnant subject in need of such treatment a uterine contracting agent capable of countering the effect, or reducing the level of nitric oxide in utero, in an amount effective to promote uterine contractions of a desired intensity and to maintain the contractions for a desired period of time, and optionally induce parturition.

Uterine contracting agents suitable for use in this variation of the invention are capable of potentiating the effect, or decreasing the level, of nitric oxide in utero include nitric oxide synthetase inhibitors such as $N^{\omega}$-nitro-L-arginine (L-NA) and analogues thereof, and $N^{\omega}$ methylarginine (NMA) and analogues thereof, $N^{\omega}$-monomethyl arginine (L-NMMA), $N^{\omega}$-nitro-L-arginine methyl ester (L-NAME), and other similar acting agents, and mixtures thereof.

The uterine contracting agents discussed above may be present in the composition in an amount of about 0.01 to 99 wt %, and more preferably about 0.1 to 85 wt %. However, other amounts of uterine contracting agents may also be used. Amounts which are suitable for specific uterine contracting agents of the invention are set forth below.

Within the context of this invention, a nitric oxide synthetase inhibitor is defined as any compound or combination of compounds capable of inhibiting the nitric oxide synthetase catalyzed conversion of L-arginine to nitric oxide and citrulline.

LNA and similar acting compounds may be present in the composition in an amount of about 0.2 to 23 wt %, and preferably about 1 to 12 wt %. NMA and similar acting compounds may be present in the composition in an amount of about 0.2 to 23 wt %, and more preferably about 1.5 to 15 wt %. Methylene blue, and its analogues and similar acting compounds may be present in the composition in an amount of about 1 to 25 wt %, and more preferably about 1.5 to 12 wt %. N-methyl arginine and similar acting compounds may be present in the composition in an amount of about 0.2 to 23 wt %, and more preferably about 1.5 to 15 wt %. Nitro-arginine methyl ester and similar acting compounds may be present in the composition in an amount of about 0.2 to 60 wt %, and more preferably about 3 to 30 wt %. Other amounts, however, are also suitable.

Any compound that reduces the level of nitric oxide is suitable as the uterine contracting agent for use in this composition. Examples of these are described above, as are the amounts in which they may be present in the compositions of this invention.

The present composition may also include other agents that are typically used for administration to a pregnant patient in need of labor induction and/or augmentation or to counter the side effects of the ingredients present therein. Some of these are listed below. However, other agents may also be incorporated.

Suitable uterine contracting agents that are capable of reducing the levels of nitric oxide, in utero were described above. The uterine contracting agents suitable for use with this invention may be administered to the pregnant subject in an amount of about 1 to 500 mg/kg/day, and more preferably about 2 to 250 mg/kg/day. However, other amounts may also be utilized as determined by a practitioner.

VII. Administration

The method of the invention may be practiced by means of a single administration, or if needed, by infusion over a period of time, as considered appropriate by a practitioner. Thus, a single administration or multiple administrations, e.g., daily or at other intervals, as indicated by the practitioner, may be used.

The composition in accordance with this method may be administered orally, transdermally, subcutaneously, intravenously, intraperitoneally, intramuscularly, intranasally, rectally or intravaginally.

The composition may be in the form of a tablet, capsule, oral, liquid, implant, injectable preparation, suppository, ointment, cream, patch, sponge, suspension, emulsion, or other formulation suitable for iontophoresis.

The composition of the invention may be prepared by powdering the various desired compounds, and optionally the carrier as is known in the art. In the use of a liquid delivery system, the compounds may be dissolved in a liquid carrier and the like. In the case of a cream or an ointment, the various carriers are blended with the compounds so that they are suspended or dissolved therein.

The present composition may be administered to a pregnant subject alone or, be it a human or non-human mammalian subject, in conjunction with other therapies known in the art.

The method of the invention may be practiced by means of a single administration, or is needed, by infusion over a period of time as considered appropriate by a practitioner. Thus, a single administration or multiple administrations, e.g., daily or at other intervals or by infusion, as indicated by regimen developed by the practitioner, may be used. Typically, when the onset of preterm labor is noticed by one of many detection means, the practitioner may administer an initial dose of the composition of the invention as described above.

Upon further monitoring, a decision may be made as to whether further intervention is necessary or a single administration has countered the initiation of labor. If after a certain period of time, the contractions reappear, a further administration of the composition may be undertaken. The present composition may be administered for a period of time of about 1 minute to 9 months continuously in nontoxic amounts. The time for which the administration is undertaken depends on the time needed to prolong pregnancy to a number of weeks into the term that will make the fetus viable.

The nitric oxide sources may be administered in amounts, doses and intervals within the range described above. However, each individual nitric oxide source may be administered in particularly preferred ranges of dosages.

The application of the method of the invention may be discontinued when the patient reaches a point during the pregnancy term that permits parturition and the delivery of a healthy newborn.

UTILITY

The method of the present invention may be applied to subjects such as human and non-human mammalian females. Preferred use is the treatment of pregnant woman experiencing preterm labor or experiencing overterm pregnancy. Examples of non-human mammalian animals are primates, equines, bovines, ovines, porcines, canines, felines, and rodents. Examples of other animals that may benefit from the present treatment are all types of animals held in captivity such as zoo animals and pets such as canines and felines, among others. The field of animal husbandry provides a broad application for the present method.

The contractile quiescence of the uterus is essential for implantation of the fertilized ovum and for maintenance of pregnancy. Despite numerous studies attempting to understand the changes that initiate parturition at term, little had been known up to the present time on how labor is triggered at term, or how preterm labor arises. A conceptual obstacle has been the lack of agreement as to whether labor is the result of a new process initiated at term or the termination of a process maintained throughout gestation. The latter concept is favored primarily because it is more consistent with the observation that the pregnant uterus remains quite refractory to a variety of stimuli. This suggests an active inhibition of contractions, which normally subsides at term. While the endogenous process by which term labor is initiated remains obscure, a more pressing clinical issue is the etiology of preterm labor. Preterm labor represents a disruption of the uterine quiescence that characterizes normal gestation. It is widely known that as a consequence of early parturition, preterm labor usually increases the rate of morbidity and mortality in neonates.

Administration of compounds that increase the level of nitric oxide in utero or enhancers of expression of iNOS to a pregnant female, results in uterine relaxation. This invention, therefore, provides the use of pharmacological agents capable of increasing the level of nitric oxide sources in utero as an effective treatment for preterm labor.

EXAMPLE 1

A Non-Human Primate model for Study of Preterm Labor

This example illustrates a non-human primate model used for study of preterm labor.

The chronic vested, awake monkey has the incidence of spontaneous preterm labor and delivery similar to that observed in humans. To effectively study the effect of various agents on preterm labor, its inhibition or induction, it was necessary to assure that the model allows to continuously follow, in the awake monkey, uterine EMG to observe the frequency and strength of contractions, intrauterine pressure, maternal arterial pressure, blood flow to the uterus, as well as dynamics of the drug delivery across the placenta and drug levels on either maternal or the fetal side of placental.

Five time-mated pregnant rhesus (Macaca mulatta) monkeys having gestational ages between 106–137 days and expected term at 165 days were obtained from the California Primate Research Center.

Under general anesthesia with a halogenated agent, polyvinyl fluid-filled catheters for pressure transduction were placed in the maternal common femoral artery, the hypogastric artery, and the intra-amniotic cavity. An ultrasonic flow probe was placed around the left hypogastric artery. A polyvinyl catheter in the common femoral vein was used for infusions. All the catheters were tunneled subcutaneously to the back where they exited into a vest and steel tether system. A radiotelemeter with two electrodes was placed 1 cm apart on the uterine fundus continuously transmitted the uterine electromyogram (EMG) with a high signal-to-noise ratio.

Maternal hysterotomy for placement of monitors and catheters consistently initiated uterine irritability, usually more intense at night, which progressed to organized labor over several days. As labor progressed, the uterine EMG tracings evolved from diffuse random spikes associated with small increases in intrauterine pressure into organized, fusiform shaped complexes associated with high amplitude pressure increases. A uterine contractility index, similar to Montevideo units (*Am. J. Ob. Gyn.*, 157:1487–1495 (1987)), derived by integrating the area under the intrauterine pressure curve in 10-minute intervals was used to quantitate labor and showed that it progressively increased until the membranes ruptured and the fetus was delivered.

Active labor was induced by hysterotomy as described above or by administration of labor inducing drugs such as progestins. All monkeys were studies in the awake state after recovery from anesthesia and after confirmation of active labor by assessment of their contractility index by continuously monitoring of all variables. The progression of labor, as reflected by both electrical and mechanical activity of the uterus, was followed, as well as progression to full labor, rupture of membranes, and delivery.

In all in vivo studies, simultaneously recorded EMG's and intrauterine pressure tracings were continuously acquired in real time utilizing the LABVIEW® data flow processing software (National Instruments, Austin, Tex.) on an Apple computer. The LABVIEW® system is capable of defining the characteristics of the uterine EMG that would correlate with significant uterine contractions and excluding those waveforms that do not correlate with significant uterine contractions. The resulting data were used to monitor EMG activity to determine the strength, frequency, and severity of labor.

Short-term fetal and maternal toxicity of tested drugs was monitored by continuous assessment of both maternal and fetal physiologic parameters such as blood pressure, blood flow distribution using flow distribution using flow probes, heart rate, cardiac output, and oxygenation. The fetal hemodynamic response to various agents was assessed noninvasively by echocardiographic and Doppler ultrasound measurements of pulsatility index, cardiac contractility, and cardiac output. The long-term effect of any tested drug on fetal and neonatal growth and development was assessed by following infant monkeys that have been delivered after treatment of the mother with these drugs.

EXAMPLE 2

Determination of Inhibitory Activity of S-Nitroso-N-Acetylpenicillamine on Preterm Labor in Monkeys This example illustrates testing of various S-nitroso-N-acetylpenicillamine (SNAP) on ablation of preterm labor.

SNAP was synthesized by nitrosylation of N-acetylpenicillamine as described in *J. Pharmacol. Exp. Ther.*, 255:1256–1264 (1990).

Group 1. In the first group, four monkeys were treated as described in Example 1. When the labor contractions occurred in about 1 minute intervals reaching the uterine contractility index of about 70 mm Hg/sec., animals were either infused with SNAP (experimental animals) or with normal saline or N-acetylpenicillamine in DMSO (control animals). Infused animals received 0.5–4.0 ml/min. of 0.2 mg/ml of S-nitroso-N-acetylpenicillamine (SNAP) and corresponding for 30 minutes at a time. The infusion of SNAP at any time in the progression from uterine quiescence to full labor ablated the electromyographic and mechanical activities of the contracting uterus. The infusion of SNAP into the 4 monkeys was associated with a decrease in the frequency and strength of the contractions as seen in FIG. 3. The effect of SNAP on preterm labor was found to be dose dependent.

The vasodilatory effects of SNAP, as indicated by a decrease in mean arterial pressure, and an increase in blood flow to the uterus were also found to be dose dependent.

The monkeys were given SNAP in 30 minutes doses of 0.625–40 $\mu$g/kg/min to test its dose dependency. The greatest effects were seen at 40 $\mu$g dose.

Well-established uterine contractions were diminished or ablated. Maternal mean arterial pressure decreased in a dose dependent manner. This effect was associated with an increase in hypogastric artery flow.

No significant difference was found in the effect of SNAP whether it was infused into the systemic venous circulation via the femoral vein or whether it was administered directly into the uterine circulation via the hypogastric artery.

The infusion of normal saline or N-acetylpenicillamine dissolved in dimethyl sulfoxide had no effect on the uterine contractility index or maternal hemodynamics. Thus, SNAP-induced changes in uterine contractility and material hemodynamics are mediated through nitric oxide.

Group 2. In the second group, 5 monkeys (gestational ages 118–134 days) were treated and then administered SNAP as described above. The results of the Group 2 tests confirmed the finding that at any time in the progression from quiescent uterine to full labor, SNAP ablated the electromyographic and mechanical activities of the contracting uterus. In all 5 monkeys, the infusion of SNAP (21 occasions) was always associated with decrease in the frequency and amplitude of uterine contractions.

As above, the effect of SNAP on preterm labor was dose dependent, and the vasodilatory effect of SNAP infusion, as measured by a decrease in mean arterial pressure, and an increase in blood flow to the uterus, were also dose dependent. No significant difference was found on the effect of SNAP whether it was infused into the systemic venus circulation via the femoral vein or directly into the uterine circulation via the hypogastric artery.

EXAMPLE 3

Determination of Inhibitory Activity of Various Tocolytic Agents on Preterm Labor This example illustrates inhibitory activity of other tocolytic agents on preterm labor.

Using the monkeys and general procedure of Examples 1 and 2, two monkeys were treated with papaverine. Papaverine hydrochloride was administered to monkeys as an intravenous bolus in an amount of 6 mg/kg. This was followed by the I.V. administration of papaverine by 1 mg/kg per hour intravenous infusion. Only these extremely high doses were able to lower the uterine contractility index by 85%. Papaverine HCl was obtained from Lederle.

Zaprinast was administered to 2 monkeys using the procedures of Examples 1 and 2 in an amount of 3 mg/kg intravenous bolus decreased the uterine contractility index by 35%–95%.

Amrinone, obtained from Sanofi Winthrop Pharmaceuticals was administered to 3 monkeys in amount 0.25 mg/kg as intravenous bolus showed no significant effect of these compounds on the uterine contractility index.

EXAMPLE 4

Determination of Nitric Oxide Synthase Activity in the Pregnant Rat Uterus

This example describes methods used for in vitro studies of activity of nitric oxide synthase in pregnant rat uterine tissue.

Preparation of Uterine Tissue

Uterine tissue was obtained from time-mated pregnant female Fischer rats. Animals were euthanised by ether gas overdose. The uterus was removed, fetuses, placenta and fetal membranes were separated and discarded. Uterine tissue was rinsed several times in cold isotonic saline, minced into approximately 5 mm cubes, quick frozen in liquid nitrogen and stored at $-70°$ C. for later determination of NOS activity. For morphological studies, a 1×1 cm sample of full thickness uterus was take prior to freezing and fixed for two hours in 4% paraformaldehyde then stored in 30% sucrose at 4° C. until processed as described below.

NOS Morphology Stains

Paraformaldehyde fixed full thickness uterine samples were examined for the presence of NOS using a tetrazolium blue dye. This method has specific for localizing NOS. Forty micron thick floating sections of the fixed tissue were incubated for 60 minutes at 37° C. in the presence of 0.5 mM nitro blue tetrazolium (NBT) dye and 1 mM NADPH. The formation of NBT formazan product required the presence of NADPH.

Measurement of NOS Enzyme Activity

NOS enzyme activity was quantitated using the [$^3$H]-arginine to [$^3$H]-citrulline conversion assay. Previously frozen minced rat uterus was homogenized using a Tissuemizer (Tekmar). Samples were suspended in a volume of 50 mM HEPES, 0.1 mM EDTA, 1 mM DTT, 1 μM leupeptin, 1 μM peptastatin (pH 7.5) that was four times the tissue's wet weight in grams. All homogenization and protein separation steps were performed at 4° C. Crude soluble and membranous subfractions were prepared from homogenates by differential centrifugation. The first centrifugation was performed at 1000 g for 20 minutes, followed by centrifugation of the supernatant at 30,000 g for 20 minutes. In all preparations, the supernatant (soluble fraction) was decanted at 30,000 g for 20 minutes. In all preparations, the supernatant (soluble fraction) was decanted from the pellet (membranous fraction). Pellets were then washed to remove residual soluble protein by resuspension in 5 ml of buffer and re-centrifugation. The final pellet was resuspended in 1 ml of buffer and re-centrifugation. The final pellet was resuspended in 1 ml of buffer. In one experiment purified cytosolic and microsomal subfractions were prepared for the purpose of demonstrating the relative proportion of NOS activity in these two subfractions, and to compare this with the crude separations. Homogenates were centrifuged at 10,000 g for 20 minutes and the resulting post-mitochondrial supernatant was subjected to ultracentrifugation at 105,000 g for 60 minutes.

Samples of the cellular subfractions (50 to 100 μg protein) were incubated at 37° C. for 45 minutes in the presence of 1 mM NADPH, 14 μm tetrahydrobiopterin, 5 μM FAD, 1 mM EGTA, 1 mM magnesium, 5 μM L-arginine and 15 nM [$^3$H]-arginine (Specific activity: 77 Ci/mmol). Calcium-sensitive NOS activity was determined by addition of 3 mM $CaCl_2$ (resulting in a total free calcium concentration of 2 mM), and 50 units bovine brain calmodulin (Calbiochem) to aminoguanidine (0.5 mM each) to the incubations. All reactions were stopped by dilution with ice cold stop buffer (5 mM HEPES, pH 5.0) and labeled citrulline was separated from labeled arginine by ion exchange chromatography on 1 ml columns of Dowex 50W-X8 (Na form) resin. [$^3$H]-citrulline was quantitated by scintillation coating (Safety Solve, Research Products, Inc.). Total protein concentration was determined using Coomassie reagent (Bio-Rad). Protein was dissolved in 1.5N NaOH and bovine serum albumin was the standard. Enzyme activity is reported in pmol [$^3$H]-citrulline/mg protein/minute. Data are reported as means ±SE. One way ANOVA was used to evaluate differences in enzyme activity at different times in gestations, and the 95% confidence level was used.

NADPH-diaphorase Histochemical Localization of Nitric Oxide Synthase

A full thickness biopsy of the uterus was placed immediately in 2% buffered paraformaldehyde and fixed for 2 hours. The tissue then was rinsed briefly in distilled water before immersion in 30% sucrose in 0.1M phosphate buffer (pH 7.3). The tissue may be saved at 4° C. until it is convenient to cut it. Either a cryostat or a sliding microtome was utilized for cutting sections thereof from the block. A representative 20 micron-thick section was kept and stained with Masson's trichrome for orientation later. 40 micron thick sections from each block were placed in 0.05M Tris buffer (pH 8) in tissue culture plates. The floating tissue may be stored at 4° C. for many weeks.

For the NADPH-diaphorase reaction each section was incubated in a solution containing 1 mM NADPH/0.6 mM nitroblue tetrazolium/0.3% Triton X-100 in 0.05M Tris buffer (pH 8) for 30 minutes. The reaction was stopped by replacing this solution with Tris buffer. The sections were rinsed for 30 minutes in Tris buffer, arranged under water on glass slides, air-dried, dehydrated in graded alcohols and mounted with Cytoseal.

All enzyme reactions containing protein were carried out at 37° C., 1 mM NADPH, tetrahydrobiopterin, FAD, Mg, 5 mM unlabelled L-arginine and 15 nM $^3$H-arginine and other effectors (calmodulin and calcium) under conditions which drive the reaction at maximal velocity. For all NOS activities measured, optimal concentrations of all-cofactors were tested and the $K_m$ and $V_{max}$ for the activities were determined since these could conceivably change with gestation or hormonal conditions. Enzyme activity was expressed in pmol/min/mg protein.

The co-factors, $^3$H-arginine, and protein mixtures were incubated for 30 minutes and the reaction stopped by the addition of an iced stop buffer, pH 5.0. Controls for enzyme activity have the stop buffer added to the co-factor and protein solution before incubation. $^{14}$C-citrulline was added to the stopped samples (2 ml) to monitor column recovery. The samples were then applied to columns containing 1 ml of Dowex AG50W-X8 resin, Na$^+$ form, pre-equilibrated with 1N NaOH. Titrated citrulline was resolved from substrate arginine and quantified by scintillation counting.

The Bradford assay is used to determine the concentration of total protein in all samples using bovine serum albumin is as a standard. Enzyme activity is reported in pmol/min/mg protein.

EXAMPLE 5

Effect of Nitroglycerin on Active Labor in Sheep

This example illustrates effect of nitric oxide donor nitroglycerin on inhibition of contractions during active labor in sheep and investigates the ability of one nitric oxide donor, nitroglycerine, to inhibit uterine contractions in close-to-term laboring pregnant sheep.

Four pregnant sheep (135–140 days gestation, term 145 days) instrumented with an intra-amniotic and fetal catheters for other studies were found to be in active labor. Fetal and maternal arterial blood pressures and intra-amniotic pressure were measured with Statham P23DB pressure transducers and recorded continuously on a Gould direct-writing recorder. At least two 10-minute periods of recording of active labor were made. Nitroglycerine was then infused into a maternal vein at a rate of 1–3 μg/kg maternal weight/min until contractions ceased. If little or no effect was evident after 15 min, the infusion rate was increased to 4–6 μg/kg maternal weight/min. Once rhythmic contractions had ceased, a 10-minute recording was repeated.

The hard-copy recordings of intra-amniotic pressure of the two baseline periods during contractions and the recording during the period of uterine inactivity were scanned into a Macintosh computer and the data digitized. Sequential points, at 3-second intervals, were selected for each recording, and the mean intra-amniotic pressure (mm Hg) at that point recorded for each 200 such points during the 10-minute observation period. A mean value for the 200 observations was calculated, and this represented the overall average intra-amniotic pressure over the 10-minute period. The standard deviation for the 200 observations was calculated, and this gave an estimate of the variability of intra-amniotic pressure during the 10-minute recording period. To evaluate whether there were any differences between the variability of pressure during the two baseline period, or particularly between the period of contractions recorded immediately prior to starting the nitroglycerine infusion and the quite period during nitroglycerine infusion, the variance of the standard deviation data between the two respective periods of interest were compared by two-sided F ratio analysis in all four instances, intravenous nitroglycerine, generally in doses of 1–3 µg/kg maternal weight/min, essentially abolished the regular contractions recorded immediately before.

No differences were detected between the two periods of contraction before starting the nitroglycerine infusion. In all four animals, nitroglycerine stopped the uterine contractions. The mean intra-amniotic pressure (200 observations over 10 minutes) was 8.4 mm Hg during the period of inactivity (p<0.05). More importantly, the standard deviation fell from an average of 2.65 during the contraction period to 1.2 during the period of inactivity (p<0.001).

EXAMPLE 6

Effect of Nitroglycerin on Preterm Labor in Patients After Hysterotomy

This example illustrates the effect of nitroglycerin on preterm labor in human patients following hysterotomy and fetal surgery.

Three patients were treated with indomethacin 50 mg per rectum preoperatively to block prostaglandin synthesis before an incision was made in the uterus. Indomethacin alone had never been adequate to prevent intraoperative or postoperative contractions. Anesthesia was achieved with 0.25% halothane and nitrous oxide. Patients were hydrated overnight intravenously and then, after a light general anesthesia was induced, a central venous catheter and radial artery catheter was placed for monitoring. After the patient was anesthetized and the central venous pressure (CVP) brought to 2–6 mmHg with adequate intravenous crystalloid, a nitroglycerin drip was started and the infusion increased until mean arterial pressure began to fall indicating a physiologic endpoint. The dose range necessary to achieve a physiologic effect in three patients was from 5–15 µg/kg/min. The infusion rate was adjusted throughout the intraoperative and postoperative period to keep mean arterial pressure above 65 with an adequate volume maintained manifest by a CVP from 2–6 mmHg. The intraoperative infusion ranged from 8–20 µg/kg/min. The tone of the uterus was constantly monitored by a designated member of the surgical team, and if contractions occurred the infusion rate was increased.

Mild contractions noted at the time of uterine incision responded in all three cases to increase infusion of nitroglycerin. A radiotelemeter placed in the fetus continuously recorded fetal EKG, temperature, and amniotic fluid pressure. The fetal surgical procedures were carried out according to protocols devised for correction of fetal defects. The cystic adenomatoid malformation was resected through a thoracotomy requiring 37 minutes, and the fetal diaphragmatic hernias were repaired through a two-step incision in each case requiring two hours. Nitroglycerin infusion was continued throughout the procedure. In one case, two bolus doses of intravenous terbutaline (0.25 mg) were used at the time of uterine closure. Nitroglycerin infusion was continued during closure of the uterus and the maternal abdomen, during emergence from anesthesia and extubation in the operating room, and during transport to the Fetal Intensive Care Unit (ICU). Postoperatively uterine activity was continuously monitored by radiotelemeter recording of amniotic fluid pressure, by palpation of the maternal abdomen, and by intermittent monitoring of the gravid cervix by palpation. Direct continuous measurement of intrauterine pressure by the fetal radiotelemeter allowed not only continuous recording but also continuous calculation of a derived uterine contractility index. The contractility index which was used was calculated by integrating the area under the intraamniotic pressure curve every ten minutes, and thus reflects both the intensity and frequency of contractions.

Nitroglycerin infusion ablated essentially all uterine activity during and after hysterotomy for fetal surgery. Particularly striking was the effect of nitroglycerin infusion intraoperatively where even mild contractions were ablated by simply increasing the dose. Intraoperative nitroglycerin infusion was well-tolerated and very easy to adjust the maternal mean arterial pressure and volume status reflected by the CVP. Other than bolus doses of terbutaline used in one case, no other intraoperative tocolytic was required.

The nitroglycerin infusion was found effective intraoperatively and was continued during emergence from anesthesia, extubation, and transport to the ICU, the uterus remained quiescent. In one case, the indomethacin was continued to be administered. Administration of magnesium sulfate or terbutaline were not necessary in any of treated cases and this was confirmed by continuous monitoring by the fetal radiotelemeter device. Intrauterine pressure remained 0–2 mmHg throughout the 2–4 days that the nitroglycerin infusion was continued. The patients were alert, awake, and comfortable, the only complaint was a warm, flushed vasodilated feeling and occasion mild headache.

Nitroglycerin infusion had a positive effect on uteroplacental perfusion compared to the previous regimen because uterine artery blood flow was maintained in the vasodilated, hypervolemic state. No reversal of diastolic flow in the uterine arteries was observed. The mother remained warm and well perfused as long as maternal intravascular volume was maintained with crystalloid infusion to keep the central nervous pressure above 2 mmHg. No blood transfusions were required. There were no unexpected hemodynamic perturbations throughout an otherwise uneventful postoperative course.

When the uterus remained quite after 1–3 days, the nitroglycerin infusion was gradually weaned and nitropaste or nitroglycerin patches were substitute. The patients were discharged after six days and returned home when discharged by the physician.

EXAMPLE 7

Clinical Inhibition of Preterm Labor

This example illustrates the clinical utility of the invention in individual patient's cases. The studies are performed in strict clinical setting where the pregnant patient suffers from hysterotomy induced preterm labor which would, under untreated conditions, result in premature delivery or abortion.

Abbreviations:

| | |
|---|---|
| NTG | = nitroglycerin |
| OP ROOM | = operating room |
| POD | = Post operation day |
| POST OP | = Post operation |

-continued

| | |
|---|---|
| Case 1 | |
| Diagnois: | Congenital Diaphragmatic Hernia |
| Treatment: | Maternal hysterotomy and repair hernia; partial liver resection. |
| NTG Dose: | |
| OP ROOM | 5–17 μg/kg/min IV |
| POD #0 | 17 μg/kg/min IV |
| POD #1 | 16–17 mcg/kg/min IV |
| POD #2 | 16 mcg/kg/min IV |
| Other Regimen: | |
| OP ROOM | Terbutaline 0.25 mg IV two doses |
| POD #0 | Terbutaline 0.25 mg SC at 2 pm, Indocin 50 mg PR every 4 hours |
| POD #1 | Indocin 50 mg PR one dose; |
| POD #2 | Indocin 50 mg PR one dose |
| Results: | |
| OP ROOM Post OP | Uterus very soft in operating room 2–4 uterine contractions per hour; no preterm labor. |
| Case 2 | |
| Diagnosis: | L Congenital Diaphragmatic Hernia |
| Treatment: | Maternal hysterotomy and repair of hernia |
| NTG Dose: | |
| OP ROOM | 10–20 μg/kg/hour IV |
| POD #0 | 10 μg/kg/hour IV |
| POD #1 | 5–10 μg/kg/hour IV |
| POD #2 | 0–4 μg/kg/hour IV |
| Other Regimen: | |
| OP ROOM | Terbutaline 100 μg IV 3 doses |
| POD #0 | Indocin 25 mg every 6 hours |
| POD #1 | Indocin 25 mg every 6 hours Terbutaline 0.25 SC one dose |
| POD #2 | Terbutaline pump Indocin 25 mg every 6 hours |
| Results: | |
| OP ROOM Post OP | Uterus very soft in operating room 1–3 uterine contractions per hour; no preterm labor |
| Case 3 | |
| Diagnosis: | L Congenital Diaphragmatic Hernia |
| Treatment: | Maternal hysterotomy and tracheal plug; attempted resection of liver. |
| NTG Dose: | |
| OP ROOM | 1.0–12.5 μg/kg/min IV |
| POD #0 | 9–14 μg/kg/hour IV |
| Other Regimen: | |
| OP ROOM Results: | Terbutaline 0.25 mg one dose |
| OP ROOM Post OP | Uterus very soft in operating room 6–8 uterine contractions per hour; no preterm labor. |
| Case 4 | |
| Diagnosis: | R Congenital Cystic Adenomatoid Malformation |
| Treatment: | Maternal hysterotomy and resection of lung mass. |
| NTG Dose: | |
| OP ROOM | 1–20 μg/kg/min IV |
| POD #0 | 2.5–20 μg/kg/min IV |
| POD #1 | 5–18 μg/kg/min IV |
| POD #2 | 0–8 μg/kg/min IV |
| Other Regimen: | |
| OP ROOM | Terbutaline 0.25 mg IV three doses |
| POD #0 | Terbutaline 0.25 mg SC two doses |
| POD #1 | Terbutaline 0.25 mg SC three doses Indocin 50 mg PR every 6 hours |
| POD #2 | Indocin 50 mg PR every 6 hours |
| Results: | |
| OP ROOM Post OP | Uterus very soft in operating room 0–4 uterine contractions per hour no preterm labor |
| Case 5 | |
| Diagnosis: | L Congenital Diaphragmatic Hernia |
| Treatment: | Maternal hysterotomy and tracheal occlusion |
| NTG Dose: | |
| OP ROOM | 20 μg/kg/min IV |
| POD #0 | 10 μg/kg/min IV |
| POD #1 | 1–5 μg/kg/min |
| Other Regimen: | |
| OP ROOM | Terbutaline 0.25 mg IV one dose |
| POD #1 | Indocin 50 mg PR every 6 hours |
| POD #2 | Terbutaline pump Indocin 50 mg PR every 6 hours |
| Results: | |
| OP ROOM Post OP | Uterus very soft in operating room 0–2 uterine contractions per hour no preterm labor |
| Case 6 | |
| Diagnosis: | Sacrococcygeal Teratoma |
| Treatment: | Hysterotomy and resection of SCT; Fetal demise and Fetectomy |
| NTG Dose: | |
| OP ROOM Other Regimen | 10 μg/kg/min IV |
| Results: | |
| OP ROOM | Uterus very soft in operating room |
| Case 7 | |
| Diagnosis: | L Congenital Diaphragmatic Hernia |
| Treatment: | Maternal hysterotomy and repair of hernia and tracheal plug. |
| NTG Dose: | |
| OP ROOM | 1–25 μg/kg/min IV |
| POD #0 | 13 μg/kg/min IV |
| Other Regimen: | |
| OP ROOM Results: | Terbutaline 0.25 mg SC one dose |
| OP Case 8 | Uterus very soft in operating room |
| Diagnosis: | R Congenital Cystic Adenomatoid Malformation |
| Treatment: | Hysterotomy with resection of lung mass; fetal demise. |
| NTG Dose: | |
| OP ROOM | 50 μg IV bolus three doses 100 μg IV bolus one dose |
| Other Regimen: | |
| Terbutaline Results: | 0.2 mg and 0.1 mg IV |

Uterine contractions severe with terbutaline alone. NTG added after onset of severe palpable contractions without great effect. No nitroglycerin infusion used.

EXAMPLE 8

Physiologic and Pharmacologic Manipulation of Isolated Monkey Uterine Muscle Strips This example illustrates in vitro method used for study of monkey uterine muscle strips.

Strips of uterine muscle from gravid monkeys were studied using a tissue bath myograph system. The tissue was suspended in baths containing Krebs solution at 37° C., bubbled with 95% $O_2$/5% $CO_2$. Data were obtained at one-second intervals and recorded on-line via a Macintosh computer while change in tension over time and strip chart graphics were recorded using the LABVIEW* computer program.

The uterine tissue was cut into 0.5 cm×0.5 cm strips, pre-loaded in the bath with 1 gram of tension and allowed to equilibrate for one hour prior to the beginning of the experiment. All drugs were suspended in distilled water or other solvent and appropriate vehicle controls were employed. Test drugs included L-arginine, L-NMA, L-NA, NMDA, VIP, rat cGRP, SNAP, methylene blue, M&B 22948, Rolipram, and 8-bromo-cGMP, all of which effect uterine tone by modulating the nitric oxide production-cGMP stimulation muscle relaxation process.

The data were quantitated as maximal tension and integrated area (tension×time) reported as percent change from the greatest spontaneous contraction over time. These preparations were spontaneously active and were also responsive to oxytocin, bradykinin and endothelin. Electrical field stimulation may also be investigated as a non-pharmacologic means of inducing contractions.

EXAMPLE 9

Induction of Nitric Oxide Synthase in Uterine Smooth Muscle Cells by CSF-1 and TGF-β-1

This example illustrates induction of nitric oxide synthase in uterine smooth muscle cells by cytokines CSF-1 and TGF-β-1 resulting in endogenous tocolysis.

All chemicals used in ths study were of reagent grade quality. Tritiated-arginine (69 ci/mmol) was obtained from Amersham (Arlington Heights, Ill.). Collagenase D and DNAase were obtained from Boehringer-Manheim (Indianapolis, Ind.). M-CSF-1, TGF-β1, IL-1 β, TNF-α were obtained from R and D Systems (Minneapolis, Minn.). Dexamethasone, prostaglandin E2, L-NAME, lipopolysaccharide (E. coli O55:B5) and murine γ-IF were obtained from Sigma Chemical Company (St. Louis, Mo.). Tissue culture media were obtained from the Cell Culture Facility, UCSF.

Enzymatic Dispersal of Uterine Smooth Muscle Cells

Uterine myocytes were isolated from Swiss-Webster female on days 14 to 15 of pregnancy. The uterus was removed under sterile conditions, and fetuses, membranes and placentas were discarded. The decidua was scraped from the surface of the myometrium. Uterine tissue was rinsed several times in cold isotonic saline, minced and suspended in a 1 mg/ml solution of collagenase B and 100 μg/ml DNAase in MEM-EBSS media. Tissue was lightly agitated during enzymatic incubation (37° C., 95% $O_2$ and 5% $CO_2$).

Purity of uterine muscle cell suspensions have been previously checked and found to be 95% smooth muscle cells based on a smooth muscle actin immunostaining.

Cells (150,000) were plated on 48 well Costar plates in 250 μl of culture medium (MEM-EBSS, 1% penicillin/streptomycin, 0.29 mg/ml Glutamax (GIBCO/BRL) 10% fetal calf serum (Hyclone, Logan, Utah). The cells were allowed to adhere overnight. The medium was changed at 12 hours post-plating, at which time cytokines were added and the cultures were maintained for 12 (mRNA analysis) or 24 hours (biochemical analysis). The cytokines were reconstituted in sterile phosphate-suffered saline (PBS), then diluted in culture medium for use.

Inhibitors of iNOS induction dexamethasone ($10^{-5}$M) and PGE2 ($10^{-4}$M) were added 30 minutes prior to addition of cytokines.

Cell Culture NOS Assay and Cytokine Induction

The assays were carried out in triplicate wells. Cells were treated with cytokines or vehicle for 24 hours prior to determining NOS activity. At the completion of 24 hours each well of 150k wells was incubated with 0.6 μCi of $^3$H-arginine for 45 minutes. Control wells received an inhibitor of NOS activity L-NAME ($10^{-3}$M) 15 minutes prior to the addition of $^3$H-arginine. The reaction was topped by adding ice cold Stop Buffer (50 mM HEPES, pH 5.0, containing 1 mM L-citrulline) followed by a single freeze-thaw cycle to ensure lysis of the cells. Labeled citrulline was separated from labeled arginine by ion exchange chromatography on 1 ml columns of Dowex 50W-X8 (Na form) resin. [$^3$H]-citrulline was quantitated by scintillation counting (Safety Solve, Research Products, Inc., Mount Prospect, Ill.).

NOS activity was defined as activity that was inhibited by L-NAME. Statistical analysis was by two way ANOVA with $p<0.05$ defined as significant.

RNA Preparation and Isolation

Primary uterine myocytes were obtained by enzyme dispersal, as described above and plated at a density of $5\times10^6$ cells per 10 cm Falcon plate in serum free "Tumor Media" which is a culture medium as above, without fetal calf serum (FCS) but with 0.5 mg/ml of bovine serum albumin (BSA). Cells were allowed to adhere overnight. Media was changed and cytokines or control vehicle were added and allowed to incubate for 12 hours. RNA was prepared by guanidium thiocyanate extraction as described in Anal. Biochem., 162:156–159 (1987).

Analysis of RNA by Ribonuclease Protection Assay

40 μg of precipitated RNA prepared from each of the treatment groups was used for ribonuclease protection analysis. A 370 bp iNOS cRNA probe was transcribed from a rat cDNA template corresponding to the heme-binding domain of macrophage NOS using T3 RNA polymerase (Stratagene) and [α-$^{32}$P]UTP (New England Nuclear). Hybridization of RNA probe to sample RNA, RNAase digestion and isolation of the protected fragment were done per the Ambion RPA II™ assay kit instruction manual (Ambion, Austin, Tex.). A 5% polyacrylamide-urea denaturing gel was employed to resolve protected fragments. After autoradiography, the bands were analyzed and quantified by laser densitometry using BIO-Rad model 260, (BIO-RAD, Hercules, Calif.).

EXAMPLE 10

The Methods Used for Detection of Expression of NOS Isoforms

This examples illustrates the methods used for detection of expression of NOS isoforms.

Preparation of Soluble and Membranous Particulate Subcellular Fractions

Uterine tissue was removed aseptically from the abdomen and rinsed in normal saline (4° C.) to remove blood. The vessels penetrating along the axis, the placentas and amniotic sacs were removed, and the uteri were opened along their longitudinal axis, the placentas and amniotic sacs were removed, and the uteri were rinsed again. For studies of NOS in the decidua/endometrium, the decidua was removed by scraping with a scalpel blade, repeated rinsing, and collection of the scrapings by centrifugation of the rinse solution. The tissue was then either frozen using liquid nitrogen and stored at −70° C. (enzyme assay, RNA preparation) or used without freezing. Frozen samples retained their NOS activity. Samples for Western blot were stored frozen at −70. Western blotting analyses was performed as described in *Endocrinology,* 132:1609 (1993). Samples for morphological study, in situ hybridization, immunocytochemistry and histochemistry were pinned to dental wax at physiologic length, fixed in 4% paraformaldehyde, 0.1M NaPO$_4$, pH 7.4 for 2 hours, stored overnight in 30% sucrose then imbedded in OCT and stored at −70° C. for later cryostat sectioning.

Uterine tissue was homogenized in 4 volumes/wet weight in 50 mM HEPES pH 7.6, supplemented with protease inhibitors using a Tissuemizer (2×5 sec at 80% power). Cellular debris and unbroken cells were sedimented at 1000×g, and the supernatant recentrifuged at 30,000×g to produce a crude soluble fraction, and a membrane particulate fraction. Since the enzyme activity was present in crude cellular subfractions it did not have to be extensively purified to assay. When appropriate, a 10,000×g post-mitochondrial supernatant were further processed by centrifugation at 100,000×g for 30 minutes to produce true cytosolic and microsomal membrane preparations to verify the cellular subfraction in which the NOS activity resides. The membranous subfraction was extensively washed and recentrifuged to remove any contaminating soluble activity. Extractability of the membranous activity was assessed in the presence of 1M KCl to determine whether any putative membranous activity consists of soluble activity which is associated with the membrane in a change-dependent manner as has been found for bNOS expressed in human but not rat skeletal muscle.

Nitric Oxide Synthase Activity

For most assays, enzyme activity was measured by the conversion of arginine to citrulline.

Arginase activity is a potential contaminant of the soluble NOS preparations. This activity was evaluated in the mouse and rat uterine preparations, and it has been determined that it is unlikely to complicate the NOS determinations because it is not inhibited by either aminoguanidine or L-NAME, the two NOS inhibitors which were used to define NOS activity. Further verification was done to assess the extent of ornithine production in the labeled arginine studies by HPLC separation of metabolites.

Conversion of $^3$H-arginine to $^3$H-citrulline

The assay was performed by monitoring the formation of $^3$H-citrulline from $^3$H-arginine by methods described in *BBRC,* 185:960 (1992). Enzyme reactions were carried out at 37° C. containing 50 to 300 μg of protein, 1 mM NADPH, 16 μM tetrahydrobiopterin, 5 μM FAD, 10 mM MgCl$_2$, 100 to 400 μM unlabeled L-arginine and 15 to 50 nM $^3$H-arginine (69 ci/mmol), and other effectors (calmodulin and calcium) under conditions which drive the reaction at maximal velocity. For all NOS activities measured, linearity of velocity was tested with time and protein, optimal incubation time, optimal concentrations of all cofactors and effectors, and the Km and Vmax for the activities were determined.

The cofactors, $^3$H-arginine, and protein mixtures was incubated for usually 30 minutes and the reaction stopped by the addition of ice cold Stop Buffer: 50 mM HEPES, pH 5.0, with 1 mM L-citrulline. All NOS activity was defined by the ability to be inhibited by the competitive antagonists L-NAME, NMA, LNA or aminoguanidine, the optimal concentrations of which (ca 100 to 1000 μM) was determined in preliminary experiments. Stopped samples (2 ml) were spiked with $^{14}$C-citrulline to monitor column recovery (which is generally about 70%), and applied to columns containing 1 ml of Dowex AG50W-X8 resin, Na+ form, and $^3$H citrulline was resolved from substrate arginine and quantitated by scintillation counting.

The Bradford assay in *Anal. Biochem.,* 72:248 (1976), was employed to determine the concentration of total protein in all samples. Bovine serum albumin was used as a standard. Enzyme activity was reported in pmol/min/mg protein. Validation of the Dowex chromatographic method was HPLC separation on SCX column.

EXAMPLE 11

Isolation of NOS Isoforms Present in the Uterus

This example illustrates isolation of NOS isoforms present in the uterus by PCR.

Degerate oligonucleotide primers (22 base length) homologous to a consensus nucleic acid sequence for cDNAs from rat brain, mouse macrophage, and bovine aortic endothelial NOS isoforms were constructed using Oligo software. Degenerate or non-degenerate oligonucleotide primers (ca 22 base length) homologous to specific regions of this consensus sequence were used to amplify uterine cDNA. Verification of the general specificity of chosen primers was based on the ability to amplify cDNA templates obtained for the known isoforms. Positive products were labeled an used to screen the nonpregnant and pregnant uterine cDNA libraries.

EXAMPLE 12

General Methods for Molecules Analysis of Uterine NOS

This example illustrates post-translational regulation of NOS activity.

Screening of cDNA Library and Characterization of Gene Products

Selected cDNAs were used as probes to screen for full-length clones in pregnant mouse cDNA libraries. Full-length sequences were obtained and compared at the amino acid level to the Genback data bank. Characterization of these cloned cDNAs included analysis of their expression upon injection of cRNA into *Xenopus oocytes* or transfection of the Syrian hamster myometrium (SHM) uterine myocyte line with cDNAs. Those confirmed to be NOS were studied as to their levels of expression throughout gestation using RNAase protection analysis of uterine mRNA.

Pregnant mouse uterine CDNA libraries was screened using the mouse radiolabelled cDNA as a probe. Pure lambda phage isolates was cloned into plasmids for double-stranded sequencing using method described in *PNAS* (U.S.A.), 87:8365 (1990). In-situ hybridization on thin sections, to various antisense probes from the full length uterine clone, was performed using techniques described in *Nature,* 328:80 (1987).

Proof of the identity of a putative uterine isoform of NOS included the ability to detect it in mRNA samples from a pregnant uterus using the isolated cDNA as probe, unique sequence identity, localization to uterine cells by in situ hybridization, demonstration of NOS enzyme activity of an expressed full-length cDNA, and appropriate specificity of antisera made from peptides or an expressed fusion protein. Expression of a uterine isoform was not limited to the uterus.

Ribonuclease Protection Assay

The methods for this assay have been described in *PNAS,* 87:8365 (1990). RNA (10 to 200 μg of total RNA, or 1 to 10

µg of A+mRNA) was mixed with gel purified $^{32}$P labeled antisense or sense (control) cRNA probes for NOS or a control probe such as beta-actin. Controls included the use of sense cRNA probes, omission of RNAase from samples of labeled probe alone and treatment of the probes with RNAase before hybridization. Additional positive controls used to evaluate isoform specificity were mRNA samples from macrophages, aortic endothelium, and rat cerebellum.

Northern Hybridization

The procedures for Northern Analysis have been described in *Pediatric. Res.*, 31:601 (1992). Briefly, samples of total RNA (>40 µg) or 2–20 µg of A+mRNA were denatured in formaldehyde and separated on a formaldehyde gel of 1% agarose. To ensure adequate transfer of mRNAs greater than 2 kb in length, the gel was treated briefly with NaOH, then neutralized with buffer before transfer to nylon membranes.

In situ Hybridization Histochemistry

The technique for in situ hybridization histochemistry has been described in *Molecular Cloning*, 2nd Ed., Cold Spring Harbor Laboratory, Cold Spring Harbor, (1989). Technical assistance with this method is available through the NIH-sponsored Core facility (HD 11979) of the Reproductive Endocrinology Center in the OB/GYN department, University of California at San Francisco. Controls were essential as described above for RNAase protection and also include use of labeled sense strand.

Antibody Production

Peptides representing unique amino acid sequences in the enzyme isoforms were synthesized at University of California, San Francisco, Biomolecular Resources Center and used to generate both polyclonal and monoclonal antibodies that distinguish among isoforms of NOS. Appropriately screened and affinity purified antibodies were used in Western blot, ELISA, and thin section immunostaining.

What is claimed is:

1. A method for control, treatment, and management of preterm labor by endogenously inducing an inhibition of preterm labor, said method comprising a step of:

administering to a pregnant mammal experiencing preterm labor a composition consisting essentially of one or more compounds augmenting an inducible nitric oxide synthase (iNOS) production in an amount effective to endogenously inhibit preterm labor.

2. The method of claim 1 wherein said compound is a cytokine alone or in combination with a progestin.

3. The method of claim 2 wherein said cytokine or a combination thereof with the progestin has an uterine-selective effect on inducing or up-regulating the expression of inducible nitric oxide synthase in the myometrium.

4. The method of claim 3 wherein the cytokine is selected from the group consisting of interferon gamma, interleukin-1 β, interleukin-6, interleukin-8, tumor necrosis factor alpha, colony stimulating factor and transforming growth factor β.

5. The method of claim 4 wherein the cytokine is administered orally, intravenously, intravaginally, intraperitoneally, transdermally, subcutaneously, intramuscularly, intranasally, rectally or intravaginally.

6. The method of claim 3 wherein the cytokine is administered intravenously by infusion.

7. The method of claim 6 wherein the cytokine is colony stimulating factor-1.

8. The method of claim 6 wherein the cytokine is transforming growth factor-β.

9. The method of claim 6 wherein the cytokine is interleukin-1β.

10. The method of claim 6 wherein the cytokine is interferon gamma.

11. The method of claim 6 wherein the cytokine is interleukin-6.

12. The method of claim 6 wherein the cytokine is tumor necrosis factor alpha.

13. The method of claim 3 wherein the cytokine is the growth factor selected from the group consisting of epidermal growth factor and fibroblast growth factor.

14. The method of claim 3 wherein said progestin is progesterone present in the composition in an amount of about 0.5–30 wt %.

15. A method for control, treatment and management of preterm labor by endogenous inducement of preterm labor inhibition, said method comprising administering to a pregnant mammal experiencing preterm labor a composition comprising an agent which activates the expression of transcriptional regulatory protein controlling the expression of gene encoding an inducible nitric oxide synthase (iNOS), thereby augmenting uterine nitric oxide production, wherein said nitric oxide is produced in an amount effective to endogenously inhibit preterm labor.

16. The method of claim 15 wherein the uterine nitric oxide production is augmented by activation of transcription of inducible nitric oxide synthase (iNOS).

17. The method of claim 16 wherein the agent induces transcription of iNOS by activating the expression of transcriptional regulating protein controlling the expression of a gene encoding iNOS transcription.

18. The method of claim 17 wherein the transcriptional regulating protein activating transcription of iNOS is activator protein-1, octamer protein-1, octamer binding protein-2 or gamma-activation factor.

19. The method of claim 1 wherein the transcriptional regulating protein is nuclear factor kappa B Jun/fos.

20. The method of claim 1 wherein the agent is tumor necrosis factor £ (TNF-d).

* * * * *